(12) United States Patent
Rohr et al.

(10) Patent No.: US 11,224,609 B2
(45) Date of Patent: Jan. 18, 2022

(54) MITHRAMYCIN DERIVATIVES HAVING INCREASED SELECTIVITY AND ANTI-CANCER ACTIVITY

(71) Applicant: University of Kentucky Research Foundation, Lexington, KY (US)

(72) Inventors: Jurgen Rohr, Lexington, KY (US); Oleg Tsodikov, Lexington, KY (US); Markos Leggas, Lexington, KY (US); Caixia Hou, Lexington, KY (US); Joseph Eckenrode, Lexington, TN (US); Prithiba Mitra, Lexington, KY (US); Abhisek Mandal, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 16/122,655

(22) Filed: Sep. 5, 2018

(65) Prior Publication Data
US 2019/0083519 A1    Mar. 21, 2019

Related U.S. Application Data

(60) Provisional application No. 62/554,422, filed on Sep. 5, 2017.

(51) Int. Cl.
*A61K 31/7056*    (2006.01)
*A61P 35/02*    (2006.01)
*A61K 31/704*    (2006.01)

(52) U.S. Cl.
CPC ........ *A61K 31/7056* (2013.01); *A61K 31/704* (2013.01); *A61P 35/02* (2018.01)

(58) Field of Classification Search
CPC .... A61K 31/7056; A61K 31/704; A61P 35/02
USPC .......................................................... 514/33
See application file for complete search history.

(56) References Cited

U.S. PATENT DOCUMENTS 9,447,135 B2    9/2016 Rohr et al.
2013/0101632 A1*    4/2013 Scott ...................... A61K 9/146
424/400

OTHER PUBLICATIONS

Weidenbach et al. (Journal of Inorganic Biochemistry 156 (2016) 40-47).*
Jia et al. (J. Org. Chem. 2006, 71, 7826-7834).*
Wohlert, S.; Kunzel, E.; Machinek, R.; Mendez, C.; Salas, J.; Rohr, J. The structure of mithramycin reinvestigated. J. Nat. Prod. 1999, 62, 119-121.
Rohr, J.; Méndez, C.; Salas, J. A. The biosynthesis of aureolic acid group antibiotics. Bioorg. Chem. 1999, 27, 41-54.
Balamuth, N., Womer, R. B.: Ewing's sarcoma, Lancet Oncol. 2010, 11, 184-192.
Delattre, O.; Zucman, J.; Plougastel, B.; Desmaze, C.; Melot, T.; Peter, M.; Kovar, H.; Joubert, I.; de Jong, P.; Rouleau, G. Gene fusion with an ETS DNA-binding domain caused by chromosome translocation in human tumours. Nature 1992, 359, 162.
May, W. A.; Arvand, A.; Thompson, A. D.; Braun, B. S.; Wright, M.; Denny, C. T. EWS/FLI1-induced manic fringe renders NIH 3T3 cells tumorigenic. Nat Genet. 1997, 17, 495-497.
Tomlins, S.A., Rhodes, D.R., Pemer, S., Dhanasekaran, S.M., Mehra, R., Sun, X.W., Varambally, S., Cao, X., Tchinda, J., Kuefer, R. and Lee, C. Recurrent fusion of TMPRSS2 and ETS transcription factor genes in prostate cancer. Science, 2005, 310,644-648.
Sastry, M.; Patel, D. J. Solution structure of the mithramycin dimer-DNA complex. Biochemistry 1993, 32, 6588-6604.
Remsing, L. L.; González, A. M.; Nur-e-Alam, M.; Fernández-Lozano, M. J.; Braña, A. F.; Rix, U.; Oliveira, M. A.; Méndez, C.; Salas, J. A.; Rohr, J. Mithramycin SK, a novel antitumor drug with improved therapeutic index, mithramycin SA, and demycarosyl-mithramycin SK: three new products generated in the mithramycin producer streptomyces argillaceus through combinatorial biosynthesis. J. Am. Chem. Soc. 2003, 125, 5745-5753.
Scott, D.; Chen, J. M.; Bae, Y.; Rohr, J Semi-synthetic mithramycin SA derivatives with improved anti-cancer activity. Chem. Biol. Drug. Des. 2013, 81, 615-624.
Leggas, M.; Eckenrode, J.; Mitra, P.; Jha, J.; Salem, S.; Mandal, A.; Thorson, J.; Rohr, J. [abstract]. In: Proceedings of the AACR-NCI-EORTC international conference: molecular targets and cancer therapeutics; Oct. 26-30, 2017; philadelphia, PA. philadelphia (PA): AACR; Mol Cancer Ther. 2018, 17 (1 Suppl):Abstract nr B043.
Hou, C.; Weidenbach, S.; Cano, K. E.; Wang, Z.; Mitra, P.; Ivanov, D. N.; Rohr, J.; Tsodikov, O. V. Structures of mithramycin analogues bound to DNA and implications for targeting transcription factor FLI1. Nucleic Acids Res. 2016, 44, 8990-9004.
Alqahtani, N.; Porwal, S. K.; James, E. D.; Bis, D. M.; Karty, J. A.; Lane, A. L.; Viswanathan, R. Synergism between genome sequencing, tandem mass spectrometry and bio-inspired synthesis reveals insights into nocardioazine B biogenesis. Org. Biomol. Chem. 2015, 13, 7177-7192.
Cardoso, A. S. P.; Marques, M. M. B.; Srinivasan, N.; Prabhakar, S.; Lobo, A. M.; Rzepa, H. S. Studies in sigmatropic rearrangements of N-prenylindole derivatives—a formal enantiomerically pure synthesis of tryprostatin B. Org. Biomol. Chem. 2006,4, 3966-3972.
Loach, R. P.; Fenton, O. S.; Amaike, K.; Siegel, D. S.; Ozkal, E.; Movassaghi, M. Derivatization of C3-alkylindoles including tryptophans and tryptamines. J. Org. Chem. 2014, 79, 11254-11263.

(Continued)

*Primary Examiner* — Shaojia A Jiang
*Assistant Examiner* — Michael C Henry
(74) *Attorney, Agent, or Firm* — Stites & Harbison PLLC; Mandy Wilson Decker

(57) ABSTRACT

Mithramycin side chain carboxylic acid (MTM-SA) derivative are provided, which include a substituted amino acid derivative, a substituted amino acid dipeptide derivative, or an unsubstituted dipeptide derivative. The MTM-SA derivatives are useful for treatment of cancer or neuro-diseases associated with an aberrant erythroblast transformation-specific transcription factor. Unique MTM-SA derivatives have increased selectively toward ETS transcription factor.

20 Claims, 3 Drawing Sheets
Specification includes a Sequence Listing.

(56) References Cited

OTHER PUBLICATIONS

Partridge, B. M.; Hartwig, J. F. Sterically controlled iodination of arenes via iridium-catalyzed C-H borylation. Org. Lett. 2012, 15, 140-143.

Feng, Y.; Holte, D.; Zoller, J.; Umemiya, S.; Simke, L. R.; Baran, P. S. Total synthesis of erruculogen and fumitremorgin a enabled by ligand-controlled CH borylation. J Am. Chem. Soc. 2015, 137, 10160-10163.

Jia, Y.; Zhu, J. Palladium-catalyzed, modular synthesis of highly functionalized indoles and tryptophans by direct annulation of substituted o-haloanilines and aldehydes. J Org. Chem. 2006, 71, 7826-7834.

Kokotos, G.; Padron, J. M.; Martin, T.; Gibbons, W. A.; Martin, V. S. A general approach to the asymmetric synthesis of unsaturated lipidic α-amino acids. The first synthesis of α-aminoarachidonic acid. J. Org. Chem. 1998, 63, 3741-3744.

Bi, W.; Bi, Y.; Xue, P.; Zhang, Y.; Gao, X.; Wang, Z.; Li, M.; Baudy-Floc'h, M.; Ngerebara, N.; Li, X. Novel β-carboline-tripeptide conjugates attenuate mesenteric ischemia/reperfusion injury in the rat. Eur. J. Med. Chem. 2011, 46, 2441-2452.

Coste, A.; Toumi, M.; Wright, K.; Razafimahaléo, V.; Couty, F.; Marrot, J.; Evano, G. Copper-catalyzed cyclization of odo-tryptophans: A straightforward synthesis of pyrroloindoles. Org. Lett. 2008, 10, 3841-3844.

Cozett, R. E.; Venter, G. A.; Gokada, M. R.; Hunter, R. Catalytic enantioselective acyl transfer: the case for 4-PPY with a C-3 carboxamide peptide auxiliary based on synthesis and modelling studies. Org. Biomol. Chem. 2016, 14, 10914-10925.

Choi, J. Y.; Calvet, C. M.; Gunatilleke, S. S.; Ruiz, C.; Cameron, M. D.; McKerrow, J. H.; Podust, L. M.; Roush, W. R. Rational development of 4-aminopyridyl-based inhibitors targeting trypanosoma cruzi CYP51 as anti-chagas agents. J. Med. Chem. 2013, 56, 7651-7668.

Osgood, C. L.; Maloney, N.; Kidd, C. G.; Kitchen-Goosen, S.; Segars, L.; Gebregiorgis, M.; Woldemichael, G. M.; He, M.; Sankar, S.; Lessnick, S. L.; Kang, M.; Smith, M.; Turner, L.; Madaj, Z. B.; Winn, M. E.; Núñez, L. E.; González-Sabín, Z.; Helman, L. J.; Moris, F.; Grohar, P. J. Identification of mithramycin analogues with improved targeting of the EWS-FLI1 transcription factor. Clin. Cancer Res. 2016, 22, 4105-4118.

Garcia-Aragoncillo, E., J. Carrillo, E. Lalli, N. Agra, G. Gomez-Lopez, A. Pestana, and J. Alonso. "DAX1, a direct target of EWS/FLI1 oncoprotein, is a principal regulator of cell-cycle progression in ewing's tumor cells." Oncogene 2008, 27, 3034-6043.

Grohar, P. J.; Woldemichael, G. M.; Griffin, L. B.; Mendoza, A.; Chen, Q.-R.; Yeung, C.; Currier, D. G.; Davis, S. Khanna, C.; Khan, J. Identification of an inhibitor of the EWS-FLI1 oncogenic transcription factor by high-throughput screening. J. Natl. Cancer Inst. 2011, 103, 962-978.

Kofman, S.; Medrek, T. J.; Alexander, R. W. Mithramycin in the treatment of embryonal cancer. Cancer 1964, 17, 938-948.

Kofman, S., Perlia, C. P, Economou, S. G. Mithramycin in the treatment of metastatic ewing's sarcoma. Cancer 1973, 31, 889-893.

\* cited by examiner

MITHRAMYCIN DERIVATIVES HAVING INCREASED SELECTIVITY AND ANTI-CANCER ACTIVITY

RELATED APPLICATIONS

This application claims priority from U.S. Provisional Application Ser. No. 62/554,422 filed Sep. 5, 2017, the entire disclosure of which is incorporated herein by this reference.

GOVERNMENT INTEREST

This invention was made with government support under grant numbers CA 091901 and GM 105977 awarded by the National Institutes of Health, and grant number PC150300 awarded by the Department of Defense. The government has certain rights in the invention.

TECHNICAL FIELD

The present disclosure relates to mithramycin side chain carboxylic acid (MTM SA) derivatives and their use in the treatment of cancers. The unique MTM SA derivative compounds disclosed herein have increased selectively toward ETS transcription factor.

BACKGROUND

All members of the erythroblast transformation-specific (ETS) transcription factor-family contain an Ets-domain, which consists of approximately 80 amino acids with four tryptophan repeats. The Ets-domain binds to double-stranded DNA of target genes containing a GGAA/T core motif and different flanking regions. Exemplary ETS transcription factors include Friend leukemia integration 1 transcription factor (FLI1) and v-ets avian erythroblastosis virus E26 oncogene-like transcription factor (ERG).

FLI1 aberrant regulation is often associated with malignant transformation and is associated with chromosomal abnormalities in humans. For example, in Ewing Sarcoma and primitive neuroectodermal tumors, a chromosomal translocation results in a chimeric EWS-FLI1 fusion protein, containing the 5' region of EWS (Ewing sarcoma breakpoint region 1) and the 3' ETS region of Fli-1 (Delattre et al., Nature. 1992 Sep. 10; 359(6391):162-5). This oncoprotein acts as an aberrant transcriptional activator with strong transforming capabilities. FLI1 and homologous transcription factors also have been implicated in human leukemias, such as Acute Myelogenous Leukemia (AML), involving loss or fusion of the tel gene, as well as other malignancies including clear-cell sarcoma, myxoid liposarcoma, desmoplastic small round cell tumor, myxoid chondrosarcoma, acute myeloid leukemia, congenital fibrosarcoma, prostate cancer and pancreatic cancer.

Another ETS transcription factor, ERG, is implicated in several cancers. Aberrant ERG regulation has been shown to be associated with diseases including Ewing sarcoma, acute myeloid leukemia (AML), prostate cancer, acute lymphoblatic leukemia (ALL), Alzheimer's disease (AD), and Down syndrome (DS).

Although ETS transcription factors such as FLI1 and ERG have been identified as critical targets in diseases such as Ewing sarcoma, no therapies have yet moved from bench to bedside that could impact the outcome of this disease. Ewing sarcoma, which affects primarily children and young adults is a difficult cancer to treat. Current therapy with a combination of severely cytotoxic drugs provides up to 60% long-term survival, but the cancer often recurs.

Mithramycin (MTM), an aureolic acid natural product previously used clinically against other cancers, was identified as a potent (low-nM) inhibitor of EWS-FLI1 in Ewing sarcoma cells (Grohar et al., (2011) Journal of the National Cancer Institute 103, 962-78). MTM exhibited similar high potency against Ewing sarcoma tumor cells in vitro and was efficacious in Ewing sarcoma mouse xenografts. Based on this study, MTM entered clinical trials at the National Cancer Institute as a Ewing sarcoma therapeutic (ClinicalTrials.gov, ID #NCT01610570) in 2012. Despite its strong inhibitory properties towards Ewing sarcoma, MTM was found to be highly toxic to non-Ewing cells, apparently because it inhibits Sp transcription factors. Therefore, MTM analogues that are more selective against Ewing sarcoma cells and/or other cancers are needed. MTM has high potential in the fight against cancer and new and improved analogues would find clinical relevance. A need thus exists to improve the performance, selectivity and efficacy of MTM.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Mithramycin (MTM; 1, FIG. 1) is an aureolic acid-type polyketide drug produced by various soil bacteria of the genus *Streptomyces* and was found to possess activity against a wide variety of human cancers.[1-2] MTM (1) was clinically evaluated in the 1960s and 70s as an agent for the chemotherapy of various cancers. As noted above, despite some remarkable success using MTM (1) as a single agent, the results were mixed due to its narrow therapeutic index and considerable variation in patients' ability to tolerate the drug.[3] Another concern was the lack of understanding of MTM's (1) mode-of-action. Taken together these limitations limited clinical use of MTM (1) as a chemotherapeutic agent and it has now been largely abandoned.[4] Interest in MTM (1) was renewed recently, after the drug was identified as the top inhibitor of the ETS transcription factor fusion, EWS-FLI1, in a screen of more than 50,000 natural products and synthetic compounds. FLI1 and ERG are ETS transcription factors that are expressed as fusions with EWS and are the primary cause of Ewing sarcoma.[5-6]

Aside from Ewing sarcoma, aberrant ETS transcription factors contribute significantly to the malignancy of prostate cancer, leukemia and lymphoma. With respect to prostate cancer, approximately 50% of patients express a truncated form of ERG as a result of the TMPRSS2 (transmembrane protease, serine 2)-ERG gene fusion.[7] Interestingly, the DNA binding domain of ERG and FLI1 is conserved and thus molecules that interfere with the activity of one should also inhibit the other. Given the importance of these aberrant transcription factors in driving malignancy, the clinical use of MTM (1) gave investigators hope for a "targeted" therapy. This was tested in a recent national cancer institute (NCI) conducted clinical study where Ewing sarcoma patients were enrolled to assess the utility of MTM (1) in a population of patients, all of whom express ETS fusions. Unfortunately, the results were inconclusive because the trial was terminated early, due to toxicities. As such, the development of less toxic and more selective analogues of MTM (1) is highly desirable.

As disclosed herein, the present inventors have identified a number of derivatives, including those identified based on mechanistic studies that focused on understanding MTM's (1) mechanism of action. At the molecular level, it is known that MTM (1) binds to GC-rich DNA as a $Mg^{2+}$coordinated dimer and modulates the activity of the transcription factor Sp1 (specificity protein 1) and presumably others.[8]

Mithramycin SA (MTMSA; 2, FIG. 1), which is a combinatorial biosynthetic analogue of MTM (1) produced by *S. argillaceus*, upon inactivation of the mtmW gene,[9] has no cytotoxicity (Table 1, Entry 19). Using the free carboxylic acid group in the 3-side chain of MTMSA, natural amino acids and small molecules were coupled to generate a series of analogues,[10] out of which MTMSA-Trp (3, FIG. 1) and MTMSA-Phe (4, FIG. 1) were found to have cytotoxicity, comparable to MTM (1).[11] It was demonstrated with crystallography studies that the 3-side chain of the MTMSA analogues can interact with FLI1.[12] In such complexes, aromatic 3-side chain MTMSA derivatives have sufficient length to directly interact with the FLI1 DNA binding domain of EWS-FLI1, reflecting the in vitro potency of MTMSA-Trp (3) and MTMSA-Phe (4) against Ewing sarcoma. Moreover, these studies pose a new mode-of-action hypothesis, which requires a ternary MTM (1)-DNA-FLI1 (or MTM (1)-DNA-ERG) complex. Disclosed herein additional, selective MTM (1) analogues for the treatment of cancers expressing aberrant ETS fusions or ETS factors. The approach combined fragment-based drug development (FBDD) with structure-activity relationship (SAR) studies starting from of MTMSA-Trp (3).

The MTM-SA derivatives disclosed herein include a substituted amino acid derivative, a substituted amino acid dipeptide derivative, or an unsubstituted dipeptide derivative. The MTM-SA derivatives are useful for treatment of cancer or neuro-diseases associated with an aberrant erythroblast transformation-specific transcription factor, as disclosed herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

BRIEF DESCRIPTION OF THE SEQUENCE LISTING

SEQ ID NO: 1 is an amino acid sequence for a DNA-binding domain (DBD) of target ETS transcription factor.

SEQ ID NO: 2 is another amino acid sequence for a DNA-binding domain (DBD) of target ETS transcription factor.

SEQ ID NO: 3 is an amino acid sequence of FLI1 transcription factor.

SEQ ID NO: 4 is an amino acid sequence of ERG transcription factor.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes MTM-SA derivatives useful for treatment of cancer and other conditions, including diseases associated with an aberrant erythroblast transformation-specific transcription factor.

Figure 1:
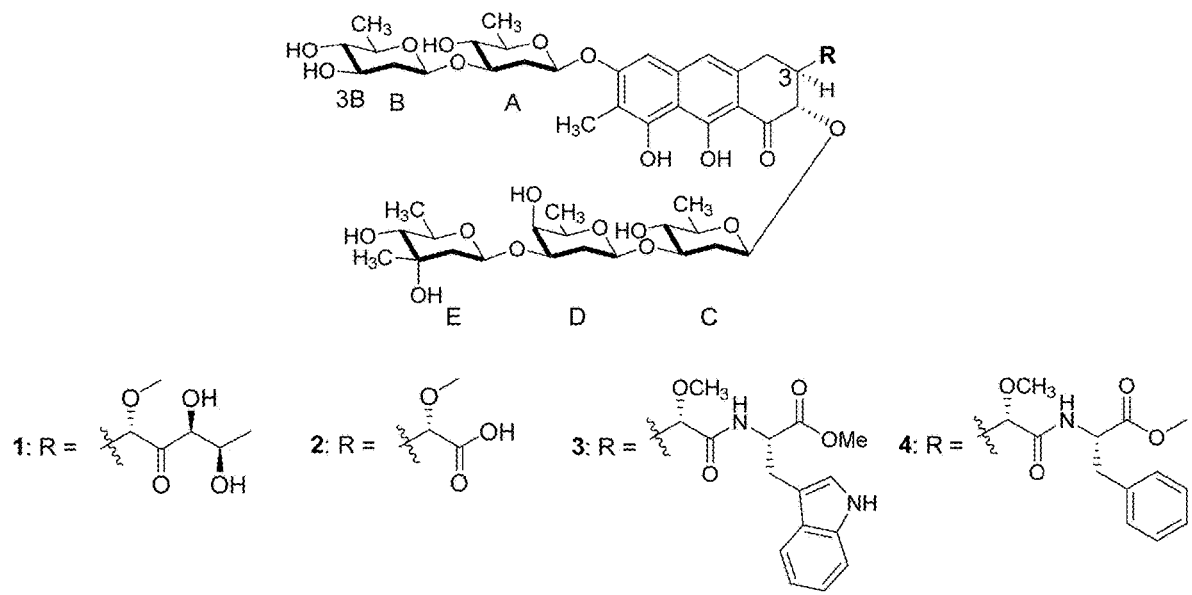
FIG. 1 includes the structure of Mithramycin (MTM; 1), Mithramycin SA (MTMSA; 2), Mithramycin SA-Tryptophan (MTMSA-Trp; 3) and Mithramycin SA Phenylalanine (MTMSA-Phe; 4)

The MTM SA derivatives of the subject technology can be synthesized according to the methods described below. The inactivation of the mtmW gene, which is the gene encoding the last acting enzyme in the MTM biosynthetic pathway, produced MTM analogues with a short side chain ketone (SK) and MTM with a short side chain diketone (SDK) (FIG. 1). Both of these analogues possess shorter side chains at the 3-position. The 3-side chain has been identified previously as important, since it is in part responsible for MTM's interaction with the DNA phosphate backbone. See U.S. Pat. No. 7,423,008. Both MTM SK and MTM SDK showed increased activity against several cancer cell lines compared to the parent MTM. These results indicate that the 3-side chain is important for the activity of MTM and offers a base for further molecular manipulations. As an unwanted side product along with the production of the desired MTM SK and MTM SDK analogues, MTM side chain carboxylic acid (SA) is also accumulated in the MtmW-minus-mutant, but showed in contrast to MTM SK and MTM SDK significantly decreased activity compared to MTM.

MTA SA is shown in formula (I) below:

Formula (II) is also represented herein as: "MTMSA-NH-R."

Thus, the A, B, C, D, E, sugars can be different from those shown, and include chain variants. Such sugars are disclosed, for example, in: (a) Baig, I.; Pérez, M.; Braña, A. F.; Gomathinayagam, R.; Damodaran, C.; Salas, J. A.; Méndez, C.; Rohr, J., Mithramycin analogues generated by combinatorial biosynthesis show improved bioactivity. *J. Nat. Prod.* 2008, 71 (2), 199-207; (b) Pérez, M.; Baig, I.; Braña, A. F.; Salas, J. A.; Rohr, J.; Méndez, C., Generation of new

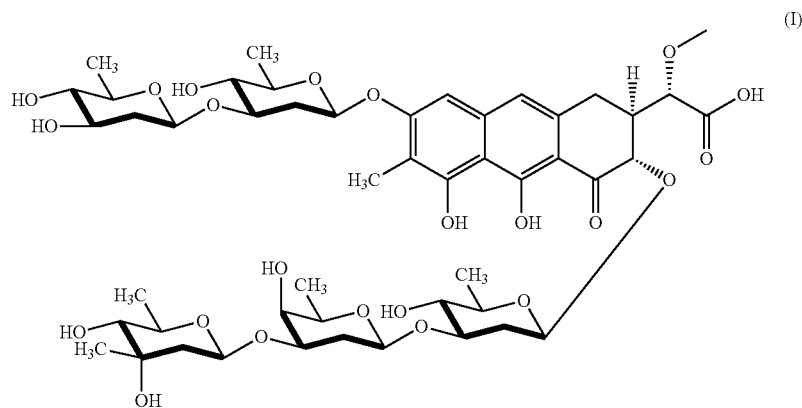

(I)

One reason for MTM-SA's decreased activity might be that its 3-side chain is too short and its negatively charged carboxylic acid does not sufficiently interact with naturally negatively charged DNA. To overcome these potential deficiencies, a semi-synthetic approach was used herein to chemically modify the unique carboxylic acid moiety of MTM SA to introduce new functionalities into the 3-side chain.

Derivatives disclosed herein are made by coupling a synthetic moiety composed of aromatic substructures, such as the substituted amino acid derivative, substituted amino acid dipeptide derivatives, unsubstituted dipeptide derivatives disclosed herein, to MTM-SA.

In one aspect of the present disclosure, the MTM-SA derivatives have the following formula (II), in which R is a synthetic moiety:

derivatives of the antitumor antibiotic mithramycin by altering the glycosylation pattern through combinatorial biosynthesis. *ChemBioChem* 2008, 9 (14), 2295-2304; (c) Nuñez, L. E.; Nybo, S. E.; Gonzalez-Sabin, J.; Pérez, M.; Ménendez, N.; Braña, A. F.; He, M.; Morís, F.; Salas, J. A.; Rohr, J.; Méndez, C., A Novel Mithramycin Analogue with High Antitumor Activity and Less Toxicity Generated by Combinatorial Biosynthesis. *J. Med. Chem.* 2012, 55, 5813-5825; (d) Remsing, L. L.; Garcia-Bernardo, J.; Gonzalez, A. M.; Künzel, E.; Rix, U.; Braña, A. F.; Bearden, D. W.; Méndez, C.; Salas, J. A.; Rohr, J., Ketopremithramycins and ketomithramycins, four new aureolic acid-type compounds obtained upon inactivation of two genes involved in the biosynthesis of the deoxysugar moieties of the antitumor drug mithramycin by *Streptomyces argillaceus*, reveal novel insights into post-PKS tailoring steps of the mithramycin biosynthetic pathway. *J. Am. Chem. Soc.* 2002, 124 (8),

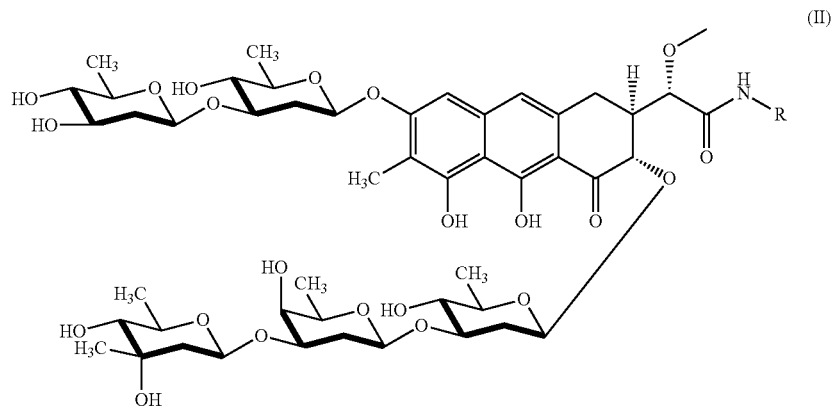

(II)

1606-1614; (e) Remsing, L. L.; Bahadori, H. R.; Carbone, G. M.; McGuffie, E. M.; Catapano, C. V.; Rohr, J., Inhibition of c-src transcription by mithramycin: structure-activity relationships of biosynthetically produced mithramycin analogues using the c-src promoter as target. *Biochemistry* 2003, 42 (27), 8313-8324. Pharmaceutically acceptable salts of the MTM SA derivative are also contemplated by the present disclosure.

In some embodiments, the MTM-SA derivative can be a substituted tryptophan (Trp) derivative. In some embodiments, the MTM-SA derivative can have the following formula (III), which can also be represented by formula (IV), in which X represents a substitution:

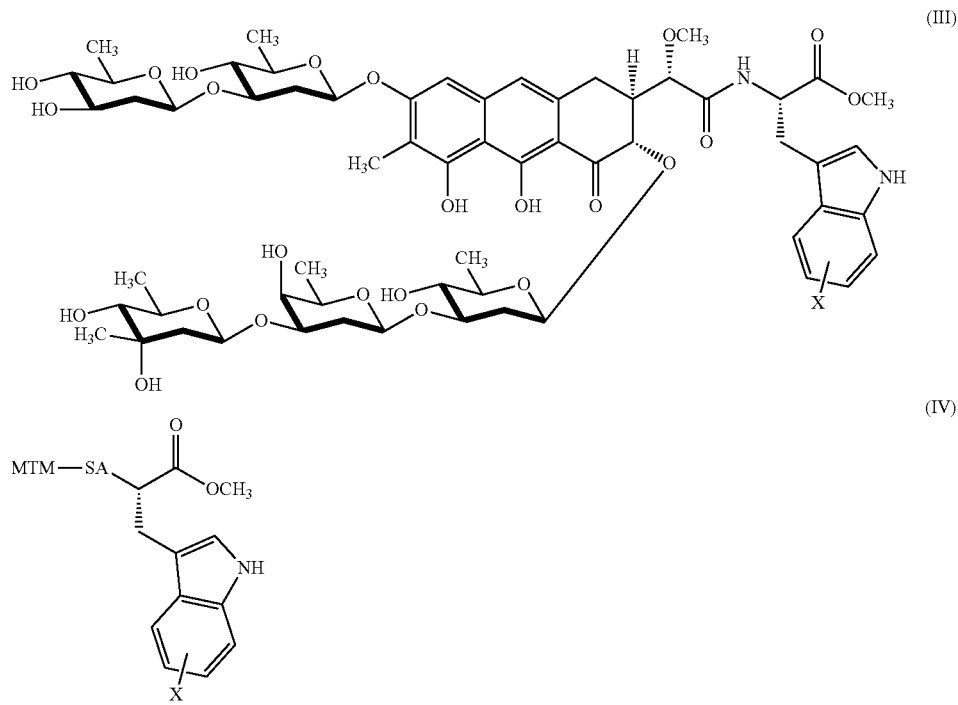

In some embodiments, the X is selected from H, lower alkyl, prenyl, aryl, alkylaryl, alkoxyl, nitro, halogen, and halocarbon. In some embodiments, X is selected from H, methyl, allyl, O-allyl, prenyl, 5,6-benzo, benzyl, phenyl, phenyl-triazole, F, and $CF_3$.

In certain embodiments, the MTM SA derivative is selected from one of the following formulae:

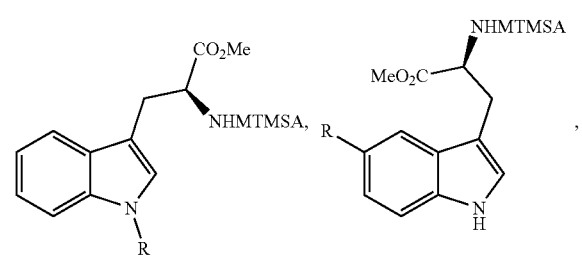

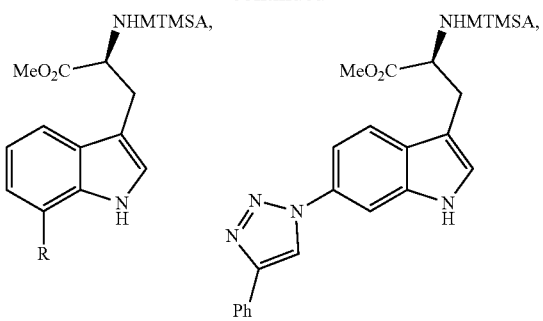

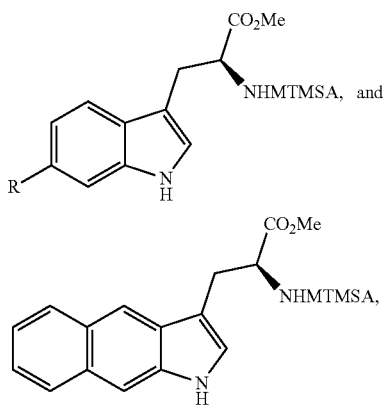

wherein R is H, methyl, allyl, O-allyl, prenyl, benzyl, phenyl, phenyl-triazole, F, or $CF_3$.

In some embodiments, the derivative has the following formula:

9

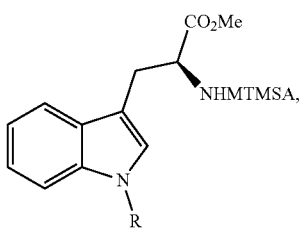

wherein R is selected from the group consisting of methyl, benzyl, allyl, and prenyl.

In some embodiments, the derivative has the following formula:

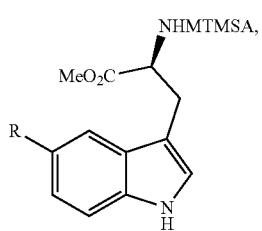

wherein R is selected from the group consisting of OMe, $NO_2$, and O-allyl.

In some embodiments, the derivative has the following formula:

10

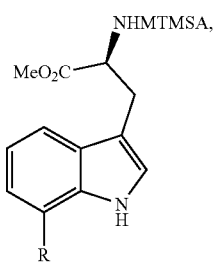

wherein R is selected from the group consisting of phenyl and allyl.

In some embodiments, the derivative has the following formula:

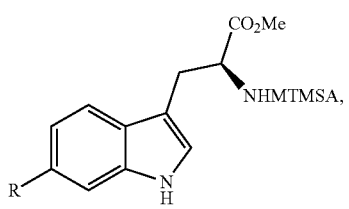

wherein R is selected from the group consisting of F and $CF_3$.

In some embodiments, the MTM-SA derivative can be a substituted phenylalanine (Phe) derivative. In some embodiments, the MTM-SA derivative can have the following formula (V), which can also be represented by formula (VI), in which Y represents a substitution:

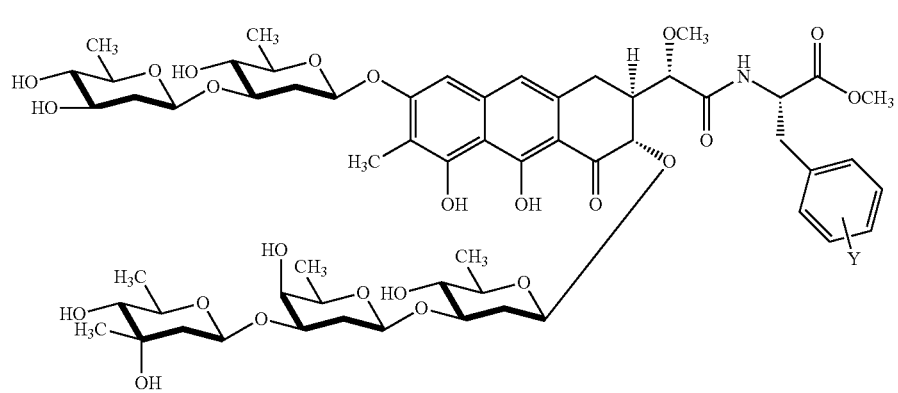

(V)

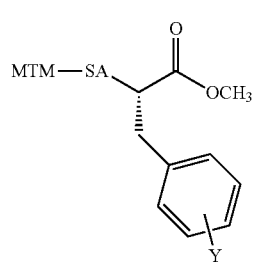

(VI)

In some embodiments, the Y is benzo. In some embodiments, the MTM-SA derivative has the following formula:

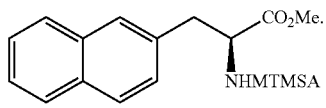

In some embodiments, the MTM-SA derivative can be a substituted amino acid dipeptide derivative or an unsubstituted dipeptide derivative. For example, the dipeptide can include Phe and Trp. In some embodiments, the derivative has one of the following formulae:

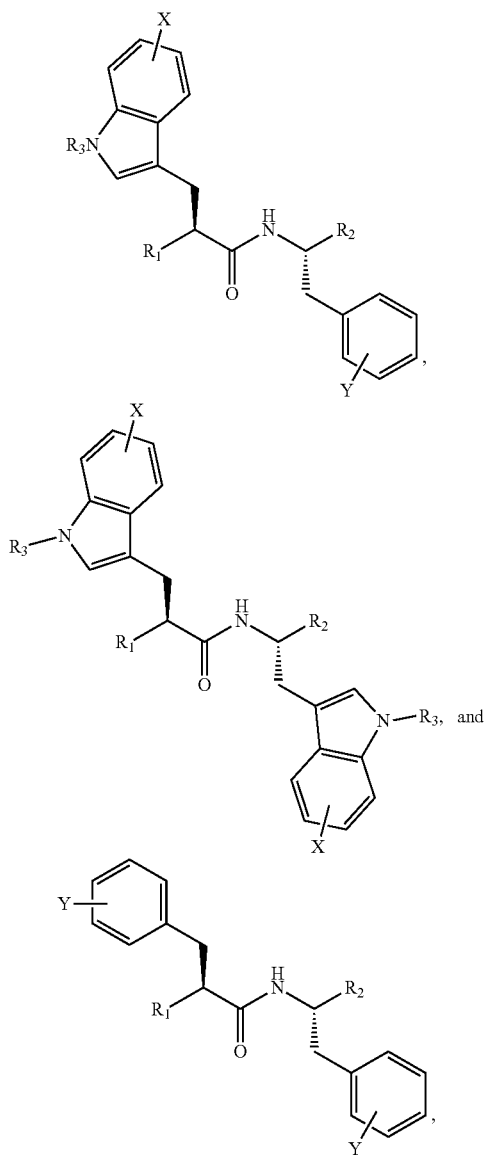

in which one of $R_1$ and $R_2$ is MTM-SA, and the other of $R_1$ and $R_2$ is $CO_2CH_3$; $R_3$ is H or Me; X is selected from the group consisting of H, methyl, allyl, O-allyl, prenyl, 5,6-benzo, benzyl, phenyl, phenyl-triazole, F, and $CF_3$; and Y is selected from the group consisting of H and 3, 4-benzo.

The MTM SA derivatives of the present disclosure can be used for the treatment of cancer, such as brain, colon, prostate, lung, breast, esophageal, pancreatic, skin, Ewing sarcoma, any type of blood cancer etc. MTM derivatives are also neuroprotective and the MTM SA derivative can be used to treat various neuro-diseases, such as Huntington disease, etc.

The biosynthesis of MTM SK and MTM SDK is accomplished through a genetically engineered *S. argillaceus* strain, M7W1, which contains an inactivated mtmW gene coding for the MtmW enzyme. Both the MTM SK and MTM SDK analogues have improved activity compared to the parent MTM compound, thus it would be optimal if these were the only two compounds produced by the M7W1 strain. However, this is not the case, and two other major compounds are produced alongside of MTM SK and MTM SDK. One of these compounds, MTM SA, has previously been disregarded as invaluable due to the relative lack of biological activity compared to the parent compound. This is unfortunate as MTM SA is produced in many fermentations in higher amounts than MTM SK or MTM SDK, and the production yield can be shifted even further in favor of the production of MTM SA by altering the pH of the culture media. Since MTM SK and MTM SDK are separated chromatographically MTM SA is easily collected and isolated alongside MTM SK and MTM SDK during the normal isolation procedure.

An aspect of the present disclosure involves targeting the 3-side chain of MTM SA to form useful MTM SA derivatives. It is known that the 3-side chain of the MTM structure is responsible for an interaction with the DNA-phosphate backbone. Thus by altering the functionality of the 3-side chain the specificity for the DNA of diseased cells can be improved. The 3-side chain of MTM SA is terminated by a carboxyl acid functional group which is likely ionized at a physiological pH, repulsing from the negative charge of the DNA phosphate backbone thereby weakening MTM SA's ability to bind to the DNA.

In one aspect of the present disclosure, side chain functionalizations were rationally selected to contain cationic amine residues in order to enhance the interaction with the DNA phosphate backbone.

Methods of Treatment

In one aspect, the subject technology provides a method for selectively modulating the activity of a target ETS transcription factor in a patient in need thereof, including administering to the patient a therapeutically effective amount of an MTM SA derivative or a pharmaceutically acceptable salt thereof, as described herein.

In an embodiment relating to this aspect, the subject technology provides a method for selectively modulating the activity of a target ETS transcription factor in a patient with Ewing sarcoma or prostate cancer for example. The method includes administering to the patient a therapeutically effective amount of the MTM SA derivative. In some embodiments relating to this aspect, the ETS transcription factor includes a DNA binding domain with an amino acid sequence that is at least 85% identical to SEQ ID NO:01 or SEQ ID NO:02 over the entire length of either of these sequences.

In another aspect, the subject technology provides a method of treating a target ETS transcription factor-mediated disease in a patient by administering to the patient a therapeutically effective amount of an MTM SA derivative described herein, wherein the MTM SA derivative specifically modulates the activity of the ETS transcription factor mediating the disease and wherein the target ETS-mediated disease is Ewing sarcoma, clear-cell sarcoma, myxoid liposarcoma, desmoplastic small round cell tumor, myxoid chondrosarcoma, acute myeloid leukemia, congenital fibrosarcoma, prostate cancer or pancreatic cancer, for example. The following Table lists several ETS transcription factors that may be modulated and associated diseases that may be treated with the subject technology.

ETS Transcription factors and associated diseases.

| Transcription factor | Disease |
|---|---|
| ETS-1 | Meningioma, invasive carcinoma of the breast, colorectal carcinoma, pancreatic carcinoma, adenocarcinoma, thyroid carcinoma, thymoma, angioma |
| ETS-2 | Breast cancer |
| ERG | TMPRSS2:ERG fusion in prostate cancer<br>EWS-ERG fusion in Ewing Sarcoma<br>ERG overexpression in AML |
| FLI1 | EWS-FLI1 fusion in Ewing Sarcoma |
| PEA3 | Invasive breast carcinoma |
| ER81 | EWS-ER81 fusion in Ewing sarcoma, prostate carcinoma, breast carcinoma |
| ELF-1 | Prostate, ovarian and breast cancers, leukemia, and lymphoma. |
| TEL/ETV6 | TEL fusion protein partners (PDGFbetaR, TRKc, ABL, and JAK2) in leukemia and fibrosarcoma |
| PU.1/SPI1 | Promyelocytic leukemia, acute myelocytic leukemia |
| Myc | Burkitt lymphoma, B-cell lymphoma, multiple myeloma, medulloblastoma, neuroblastoma, colorectal, ovarian, and intestinal cancer |

In general, the MTM SA derivatives of the present disclosure can be used for the treatment of a target ETS transcription factor-mediated disease including Ewing sarcoma, clear-cell sarcoma, myxoid liposarcoma, desmoplastic small round cell tumor, myxoid chondrosarcoma, acute myeloid leukemia, congenital fibrosarcoma, prostate cancer, pancreatic cancer, acute myeloid leukemia (AML), acute lymphoblatic leukemia (ALL), Alzheimer's disease (AD), or Down syndrome (DS) or other hyperproliferative disease in which an aberrant activity of a target ETS transcription factor is implicated. A "hyperproliferative disease" includes diseases and conditions that are associated with any sort of abnormal cell growth or abnormal growth regulation, specifically a cancer.

Some MTM derivatives are more specific than MTM for complexing with a target EST transcription factor and, therefore, inhibiting its activity. The specific or selective MTM SA derivatives of the subject technology are useful for treating diseases that are mediated by, for example, FLI1 or ERG, such as Ewing sarcoma, clear-cell sarcoma, myxoid liposarcoma, desmoplastic small round cell tumor, myxoid chondrosarcoma, acute myeloid leukemia, congenital fibrosarcoma, prostate cancer, pancreatic cancer, acute myeloid leukemia (AML), acute lymphoblastic leukemia (ALL), Alzheimer's disease (AD), or Down syndrome (DS) or other hyperproliferative disease in which an aberrant activity of a target ETS transcription factor is implicated.

Other hyperproliferative diseases which may be benefited by the methods and compounds of the subject technology include, though it is not limited to, neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In another aspect of the present disclosure, an effective amount of the MTM SA derivative or a pharmaceutically acceptable salt thereof is administered to a patient in need of cancer treatment or a neuro-disease, such as Huntington's disease. The MTM SA derivatives or pharmaceutically acceptable salts thereof of the present disclosure can be administered to a patient, e.g., a human patient, in need of such treatment by any route. The MTM SA derivatives or pharmaceutically acceptable salts thereof of the present disclosure can be administered alone or with a pharmaceutically acceptable carrier or excipient.

Dosage Form and Formulation of MTM SA

An MTM SA derivative as described herein can be administered to a patient in need thereof in any possible dosage form including, but not limited to ingestible tablets, buccal tablets, troches, capsules, elixirs, suspensions, syrups, wafers, infusion, aqueous liquid and the like. Solutions of an MTM SA can be prepared in water and mixed with suitable excipients. Under ordinary conditions of storage and use, these preparations can contain a preservative to prevent the growth of microorganisms or retain stabilization of the MTM SA derivative. The pharmaceutical forms suitable for injection include sterile aqueous solutions or dispersions and sterile powders for the extemporaneous preparation of sterile injectable solutions or dispersions. The form should be sterile and should be fluid to the extent it makes injection possible.

A composition containing an MTM SA derivative can be prepared by known methods, such that an effective quantity of the therapeutic agent is delivered to a subject. Suitable vehicles for such a composition are described, for example, in Remington's Pharmaceutical Sciences (2003) and in the Handbook of Pharmaceutical Additives (compiled by Michael and Irene Ash, Gower Publishing Limited, Aldershot, England (1995)).

In some embodiments, the composition of this disclosure enables sustained, continuous delivery of an MTM SA derivative to tissues adjacent to or distant from an administration site. The biologically-active agent is capable of providing a local or systemic biological, physiological or therapeutic effect. For example, the MTM SA derivative may act to kill cancer cells or cancer stem cells or to control or suppress tumor growth or metastasis, among other functions.

In some embodiments, the formulations of the present disclosure are administered in an amount effective to provide the desired level of biological, physiological, pharmacological and/or therapeutic effect such as inhibition of a target ETS transcription factor.

The actual dosage amount of a composition of the present disclosure administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical formulations include, for example, at least about 0.1% of an active compound, such as MTM SA or derivatives thereof or pharmaceutically acceptable salt thereof. In other embodiments, the active compound may comprise between about 1% to about 75% of the weight of the unit dosage, or between about 5% to about 50% by weight of the unit dosage, for example, and any specific percentage in between these ranges. In other non-limiting examples, a dose may also comprise from about 0.01 microgram/kg/body weight, about 50 microgram/kg/body weight, about 100 microgram/kg/body weight, about 500 microgram/kg/body weight, about 1 milligram/kg/body weight, about 5 milligram/kg/body weight, about 10 milligram/kg/body weight, about 30 milligram/kg/body weight, about 40 milligram/kg/body weight, about 50 milligram/kg/body weight, about 100 milligram/kg/body weight, or more per administration, and any range or specific amount derivable therein. In non-limiting examples of a derivable range from the numbers listed herein, a range of about 5 microgram/kg/body weight to about 5 milligram/kg/body weight, about 50 microgram/kg/body weight to about 50 milligram/kg/body weight, etc., can be administered.

For a safe and effective dosage, the formulations can be administered at an MTM SA derivative dose of about 0.01 to about 500 mg/m$^2$ (body surface)/day, about 0.01 to about 300 mg/m$^2$/day, 0.01 to about 200 mg/m$^2$/day, about 1 to about 200 mg/m$^2$/day about 10 to about 100 mg/m$^2$/day, about 25 to about 100 mg/m$^2$/day or any range derivable therein to a subject such as a human. In certain aspects, the composition may be administered at a dose of about 0.01 to about 200 mg/kg body weight, about 0.01 to about 100 mg/kg body weight, 1 to about 50 mg/kg body weight, about 1 to about 20 mg/kg body weight, about 3 to about 10 mg/kg body weight, about 3 to about 6 mg/kg body weight or any range derivable therein to a subject such as a human. In some embodiments, a formulation of the subject technology may be administered in a dose of 1, 2, 3, 4, 5, 6, 7, 8, 9, 10, 15, 20, 25, 30, 40, 50, 60, 70, 80, 90, 100 mg or more per day. Each liquid dose may be in a volume of 1, 10, 50, 100, 200, 500, 1000 or more μl or ml.

In some embodiments, the pharmaceutical formulation of the subject technology includes an MTM SA derivative in an amount effective to result in a serum concentration of the MTM SA in the mammal in a range of from 1 nM to 1 mM, particularly 1 nM to 2 μM.

Serum and systemic circulation concentrations of MTM SA derivatives effective to result in the treatment of a target ETS transcription factor-mediated disease may vary depending on a number of factors. Influential variables can include, for example, pKa, solubility or molecular weight of the MTM SA derivative. These properties of a particular MTM SA derivative may affect how a patient metabolizes the compound, how much of the compound enters and remains in the systemic circulation of the patient, and how effectively the compound treats, prevents or causes regression of the disease, e.g., Ewing sarcoma, tumor or cancer.

Precise amounts of the therapeutic composition also depend on the judgment of the practitioner and are peculiar to each individual. Factors affecting the dose include the physical and clinical state of the patient, the route of administration, the intended goal of treatment (e.g. alleviation of symptoms versus cure) and the potency, stability and toxicity of the particular therapeutic substance.

Route of Administration

In accordance with the methods of the disclosure, the described composition or formulation of the subject technology may be administered to a subject in a variety of forms depending on the selected route of administration, as will be understood by those skilled in the art. It may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, intratumoral, transepithelial, nasal, intrapulmonary, intrathecal, rectal and topical modes of administration. Parenteral administration may be by continuous infusion over a selected period of time.

Combination Therapies

In certain embodiments, the compounds, compositions or formulations of the subject technology are administered with a second or additional active agent(s) such as with one or more different MTM SA derivatives or another anticancer agent. Such therapy can be applied in the treatment of any disease for which treatment with an MTM SA derivative is contemplated. For example, the disease may be a hyperproliferative disease, such as Ewing sarcoma or prostate cancer.

In certain embodiments, the additional active agent may be a chemotherapeutic agent or a radiation therapy. Examples of chemotherapeutic agents include, but are not limited to, cetuximab (erbitux), herceptin (trastuzumab), fludarabine, cyclophosphamide, rituximab, imatinib, Dasatinib (BMS0354825), cisplatin (CDDP), carboplatin, procarbazine, mechlorethamine, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, taxol, gemcitabien, navelbine, farnesyl-protein tansferase inhibitors, transplatinum, 5-fluorouracil, vincristin, vinblastin, methotrexate, an analogue or derivative thereof. In certain embodiments, the active or anticancer agent(s) that may be used in combination with an MTM SA derivative may be fludarabine, cyclophosphamide, rituximab, imatinib or Dasatinib. In a certain aspect, the cancer may be resistant to a particular chemotherapeutic agent, such as fludarabine, cyclophosphamide, rituximab, imatinib or Dasatinib.

To facilitate an understanding of the present subject technology, a number of terms and phrases are defined below:

A reference to an element in the singular is not intended to mean "one and only one" unless specifically stated, but rather "one or more."

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Further, as used herein, the terms alkyl and/or "substituted alkyl" include an "allyl" or an "allylic group." The terms "allylic group" or "allyl" refer to the group —$CH_2HC$=$CH_2$ and derivatives thereof formed by substitution. Thus, the terms alkyl and/or substituted alkyl include allyl groups, such as but not limited to, allyl, methylallyl, di-methylallyl, and the like. The term "allylic position" or "allylic site" refers to the saturated carbon atom of an allylic group. Thus, a group, such as a hydroxyl group or other substituent group, attached at an allylic site can be referred to as "allylic."

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

As used herein, a "target ETS transcription factor" refers to a transcription factor, which comprises a DNA-binding domain (DBD) having an amino acid sequence that is at least 85% identical to SEQ ID NO: 1 or SEQ ID NO: 2 over the entire length of either of these sequences. SEQ ID NO: 1 and SEQ ID NO: 2 are set forth in an Appendix submitted herewith and incorporated herein by reference.

As used herein the term "modulator," "modulating," or "modulate" in connection with the target ETS transcription factor of the subject technology refers to any agent that has a functional effect on the transcription factor, including positively or negatively affecting its binding to a DNA substrate, positively or negatively affecting the formation and/or stability of a complex formed between the transcription factor and its oligonucleotide substrate, positively or negatively affecting its function in causing the transcription of its oligonucleotide substrate.

As used herein, the term "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "variant" in relation to the amino acid sequence of the ETS transcription factors refers to a naturally occurring allelic variant of the ETS transcription factors such as those shown in SEQ ID NO: 3 and SEQ ID NO: 4, which includes any substitution of, variation of, modification of, replacement of, deletion of or addition of one (or more) amino acids provided the resultant ETS transcription factor has a transcription factor activity and has a DNA binding domain that is at least 85% identical to SEQ ID NO: 1 or SEQ ID NO: 2 over the entire length of either of these sequences. For example, a variant of ETS transcription factor may have at least 50%, or at least 60%, or at least 70% sequence identity with the ETS transcription factors such as those shown in SEQ ID NO: 3 and SEQ ID NO: 4 over the entire length of the sequence, provided that the variant has a transcription factor activity and has a DNA binding domain that is at least 85%, at least 90%, at least 95% or at least 98% identical to SEQ ID NO: 1 or SEQ ID NO: 2 over the entire length of either of these sequences.

The terms "percentage of sequence identity" or "percentage homology" and any equivalent terms are used interchangeably herein to refer to comparisons among polynucleotides and polypeptides, and are determined by comparing two optimally aligned sequences over a comparison window, wherein the portion of the oligonucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Identity is evaluated using any of the variety of sequence comparison algorithms and programs known in the art. Such algorithms and programs include, but are by no means limited to, TBLASTN, BLASTP, FASTA, TFASTA, CLUSTALW, FASTDB [Pearson and Lipman, (1988), Proc. Natl. Acad. Sci. USA 85(8): 2444-2448; Altschul et al., (1990), J. Mol. Biol. 215(3):403-410; Thompson et al. (1994), Nucleic Acids. Res. 22(2): 4673-4680; Higgins et al., (1996), Meth. Enzymol. 266:383-402; Altschul et al., (1993), Nature Genetics 3:266-272; Brutlag et al. (1990) Comp. App. Biosci. 6:237-24], the disclosures of which are incorporated by reference in their entireties. In an embodiment, protein and nucleic acid sequence identities are evaluated using the Basic Local Alignment Search Tool ("BLAST") which is well known in the art [e.g., Karlin and Altschul, (1990), Proc. Natl. Acad. Sci. USA 87:2267-2268; Altschul et al., (1997), Nuc. Acids Res. 25:3389-3402] the disclosures of which are incorporated by reference in their entireties.

As used herein, an "oligonucleotide substrate" in reference to a substrate of a target ETS transcription factor refers to an oligonucleotide which comprises a target ETS transcription factor binding site. An oligonucleotide substrate can be single-stranded, double-stranded, or a hairpin. Preferably, an oligonucleotide substrate is double stranded. An oligonucleotide substrate can be DNA, RNA or a chimeric (comprising both deoxy and ribose nucleotides) or comprise one or more oligonucleotide modifications described herein.

As used herein, the term "transcription factor binding site" refers to a nucleic acid sequence that is recognized and bound by a transcription factor and mediates the transactivation of a reporter gene in response to that binding. Without limitations, a transcription binding site can be from any of various species including human, mouse, rat, guinea pig and the like. In some embodiments, the transcription factor binding site is a target ETS binding site such as a FLI1 binding site or an ERG binding site.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±5%, in some embodiments ±1%, in some embodiments ±0.5%, in some embodiments ±0.1%, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Initial pharmacological studies showed that both, MTMSA-Trp (3) and MTMSA-Phe (4), appeared to have the potential to overcome the limitation of MTM (1), with MTMSA-Trp (3) being the more cytotoxic of the two derivatives (Table 3, Entry 10).[11] However, their selectivity towards Ewing sarcoma cell lines were only slightly improved compared to MTM (1) (Table 3). MTMSA-Trp (3) was selected as a starting point to better understand and improve its potential binding properties to EWS-FLI1, by varying its electronic, steric and hydrogen bonding properties of tryptophan residue, with the major objective to increase the selectivity of it towards Ewing sarcoma cell lines while maintaining a cytotoxic activity comparable to MTM (1).

Scheme 1. Selective indole N-alkylation of tryptophan

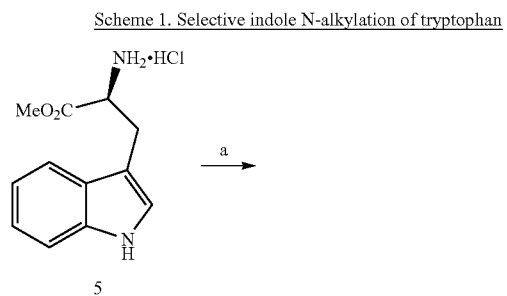

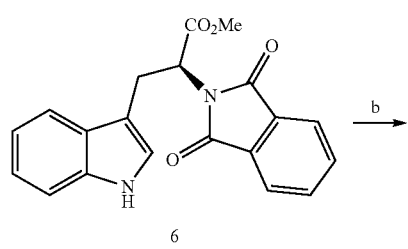

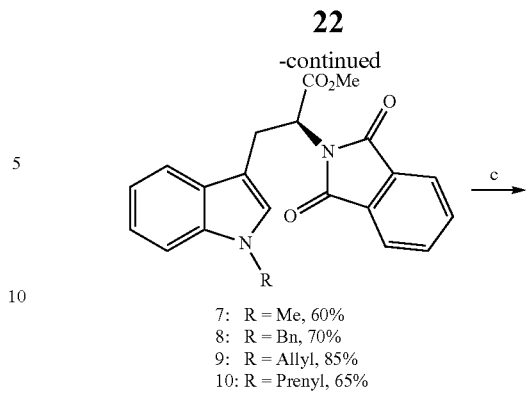

7: R = Me, 60%
8: R = Bn, 70%
9: R = Allyl, 85%
10: R = Prenyl, 65%

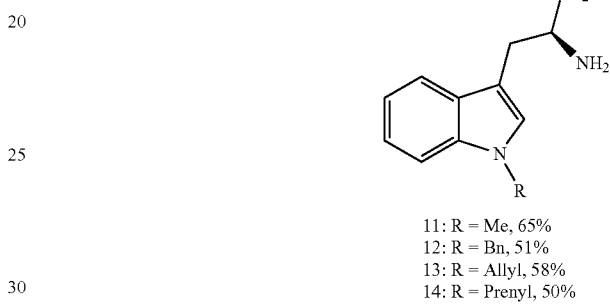

11: R = Me, 65%
12: R = Bn, 51%
13: R = Allyl, 58%
14: R = Prenyl, 50%

Reagents and conditions: a) Phthalic anhydride, Et$_3$N, toluene, reflux, 15 h, 80%;
b) NaH, Alkyl bromide, DMF (dimethylformamide), 0° C. to rt, 10 h;
c) NH$_2$NH$_2$·H$_2$O, MeOH — DCM (dichloromethane), rt.

To evaluate a potential hydrogen bonding of the indole-NH, it was protected by N-alkylation. After initial protection of the primary amine group of L-tryptophan hydrochloride (5) with phthalimide using phthalic anhydride in the presence of excess triethylamine in refluxing toluene, which gave the protected tryptophan 6[13] in 80% yield, the indole N-methylation of 6 with MeI-NaH in DMF provided 7[19] in 60% yield, and benzylation with benzyl bromide under similar conditions furnished N-benzylated tryptophan 8 in 70% yield (Scheme 1). Likewise, treatment with allyl bromide and prenyl bromide gave N-allyl tryptophan 9 and N-prenyl tryptophan 10,[14] respectively. Treatment with hydrazine hydrate in MeOH-DCM at room temperature ensured the removal of the phthalimide protection group in all cases (7-10), to provide the corresponding amines (11-14) in 50-65% yield (Scheme 1).

To diversify the tryptophan residue, iridium-catalyzed borylation and palladium catalyzed cross-coupling reactions were applied. Borylation allowed the introduction of various functionalities into the indole core of tryptophan, since the carbon-boron bond can be easily modified. For the C7 diversification of tryptophan, the required borylated tryptophan 15[15] was prepared following the method developed by Movagasshi and co-workers starting from protected tryptophan 16 (Scheme 2). To incorporate an allyl residue into tryptophan, which could serve as a handle for further modifications through Grubbs chemistry, 7-allyltryptophan 17 was chosen.

Scheme 2. C7 Functionalization of tryptophan using iridium catalyzed borylation chemistry.

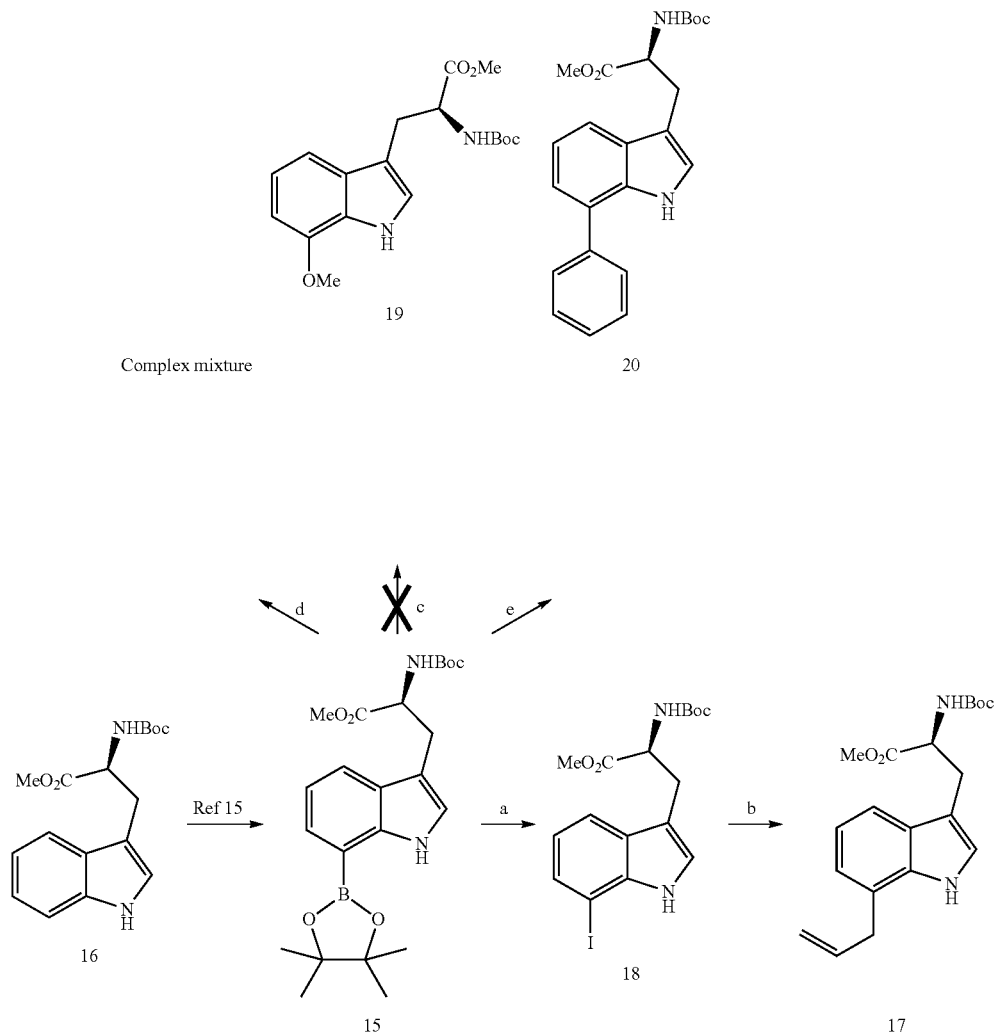

Reagents and conditions: a) CuI, 1,10-Phen, KI, MeOH—H₂O, 40%; b) Allyl(n-Bu)₃Sn, Pd(PPh₃)₄, PhMe, 120° C., 60%; c) MeOH, Cu(OAc)₂; H₂O, Et₃N, O₂, rt 12 h; d) CuTC, Togni reagent, 1,10-Phen, DCM, LiOH, H₂O, rt; e) Pd₂(dba)₃, SPhos, K₃PO₄, PhI, PhMe, 80° C., 70%.

Borylated tryptophan 15 was treated with potassium iodide in the presence of CuI as the catalyst and 1,10-phenanthroline as the ligand[16] to avail 7-iodotryptophan 18, which upon Stille coupling reaction with allyltributylstannane furnished the allyltryptophan derivative 17 in 60% yield (Scheme 2). Chen-Lam coupling of 15 failed to provide an electron enriched methoxytryptophan 19. Trifluoromethylation of 15 using the Togni reagent produced a complex mixture, possibly because of the interference of the free indole-NH. However, Suzuki coupling reaction of 15 with iodobenzene in the presence of Pd₂(dba)₃ as the catalyst resulted in 7-phenyltryptophan 20 in 70% yield (Scheme 2).

Scheme 3. C6 Functionalization of tryptophan using iridium catalyzed borylation chemistry

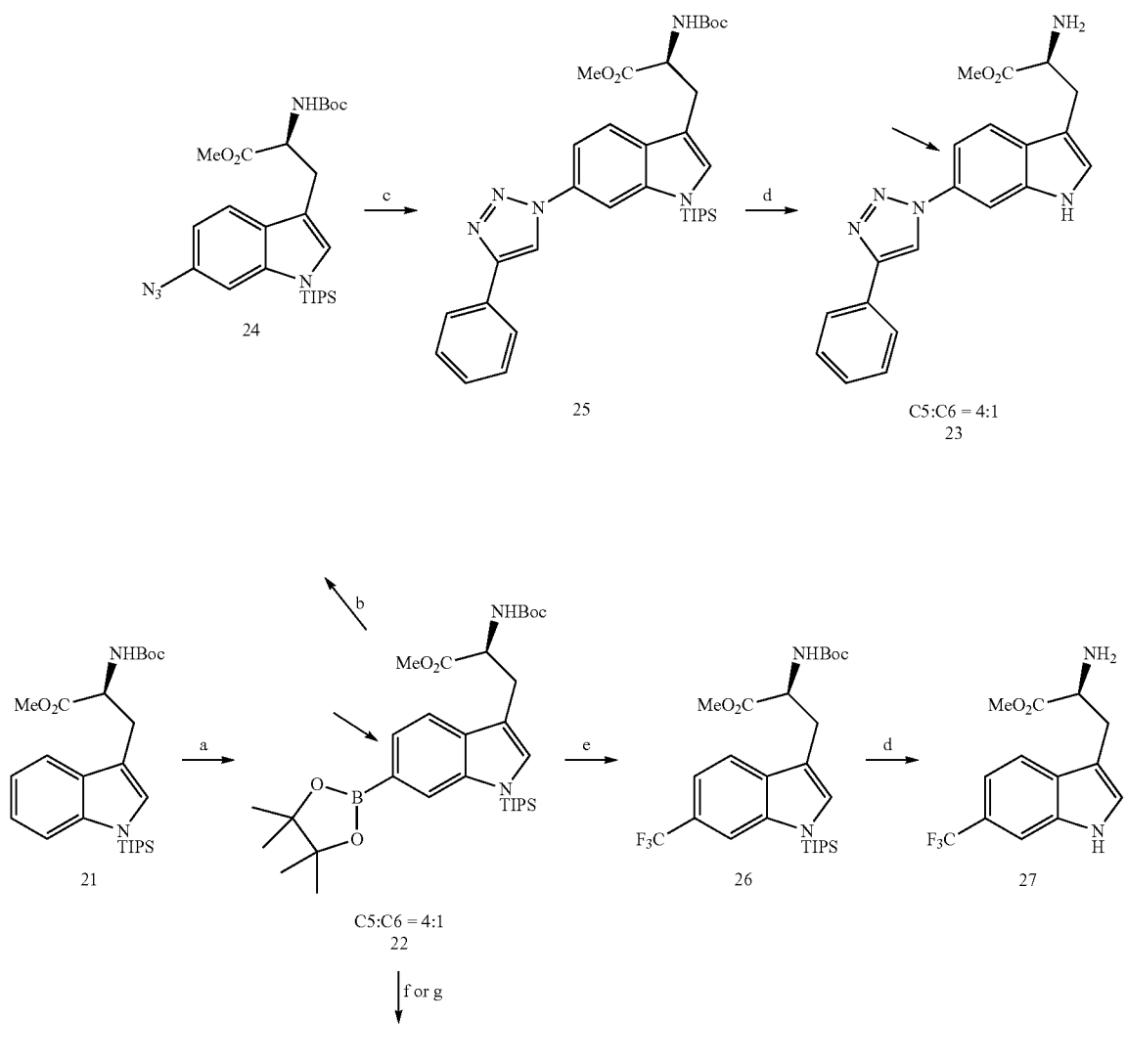

Reagents and conditions: a) Ir[(cod)OMe]$_2$ (5 mol%), phenanthroline (10 mol%), HBPin (0.25 equiv), B$_2$Pin$_2$ (4.0 equiv), hexane, 80° C., 70%; b) NaN$_3$, Cu(OAc)$_2$•H$_2$O, MeOH, 70%; c) Phenyl acetylene, CuI, DIPA, HOAc, DCM, 72%; d) 4N aq HCl, EtOAc, rt, 4 h; TBAF, THF, rt, 2 h, 85% (2 Steps); e) CuTC, Togni reagent, 1,10-Phen, DCM, LiOH, H$_2$O, rt, 60%; f) Cu(OTf)$_2$, KF; g) AgOTf, NaOH, Selectflour.

Functionalization of C6 of tryptophan was achieved by following a recently developed borylation of tryptophan 21 by Baran et al.,[17] which provided an inseparable 4:1 mixture of C6 and C5 borylated Trp 22[17] (Scheme 3). Treatment of the borylated tryptophan 22 with sodium azide in the presence of Cu(II) acetate as the catalyst produced 6-azido tryptophan 24 in good yield, which under Cu(I) catalyzed click chemistry conditions provided the triazolyl-phenyl-tryptophan 25 in 72% yield. After removal[17] of the tert-butyl carbamate and triisopropyl silyl protection, the triazolyl-phenyltryptophan free amine 23 was obtained in excellent yield. Trifluoromethylation of 22 using the Togni reagent successfully yielded an inseparable mixture of C5 and C6 trifluoromethlytated tryptophan 26 in 60% combined yield, complementing the requirement of the indole-NH protection. However, fluorination of 22 remained inaccessible under both nucleophilic and electrophilic conditions, owing to the labile nature of the triisopropyl silyl group (Scheme 3).

Scheme 4. Palladium catalyzed tryptophan synthesis

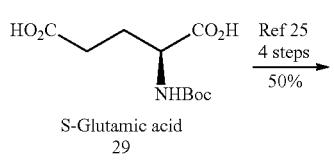

S-Glutamic acid
29

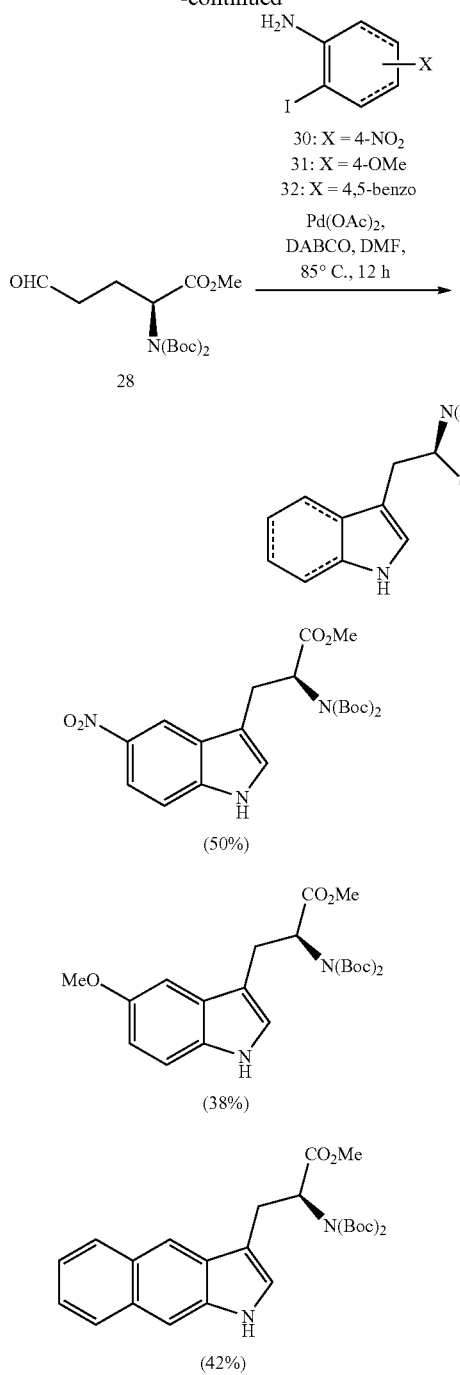

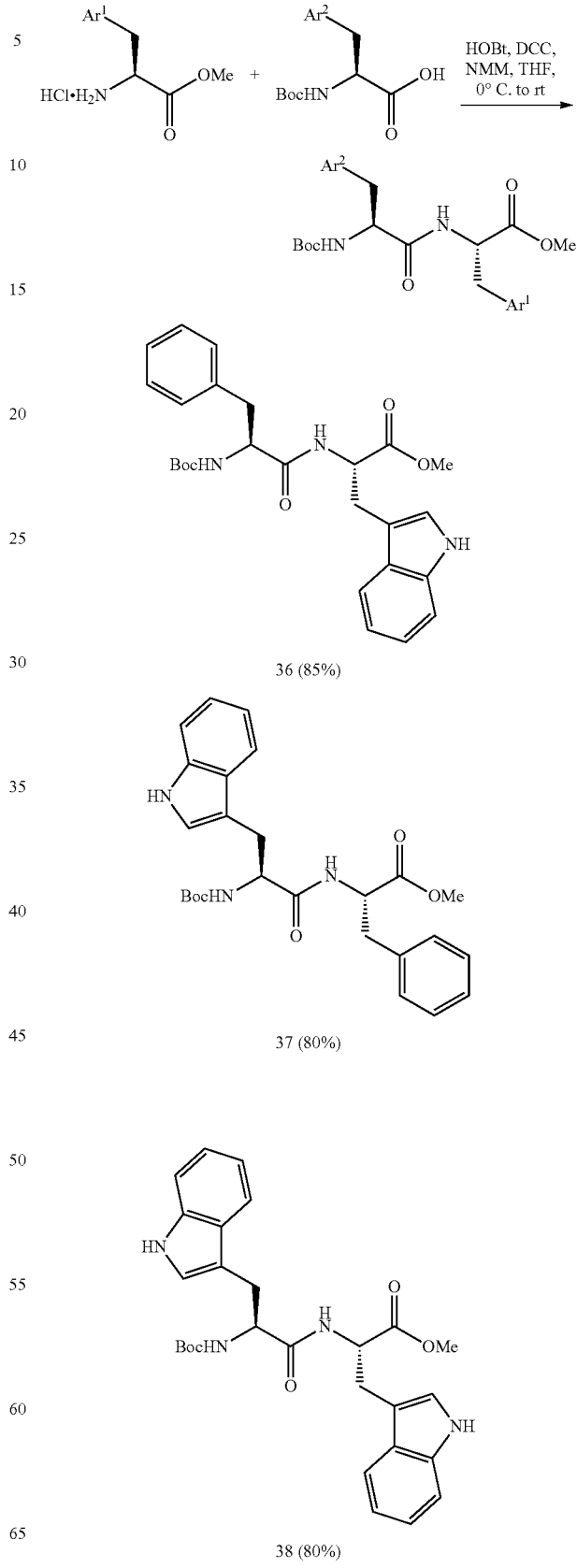

Scheme 5. Synthesis of select dipeptides by HOBt-DCC coupling

The palladium catalyzed tryptophan synthesis[18] methodology was utilized to access electron rich and electron deficient tryptophan residues. The required aldehyde 28[19] was prepared from S-glutamic acid in 4 steps, subjected to the palladium catalyzed intramolecular cross-coupling reaction with three 2-iodoaniline derivatives(30 to 32) in the presence of palladium acetate as the catalyst and DABCO as the base. The reaction yielded 4-nitrotryptophan 33[18] (50%), 4-methoxytryptophan 34[18] (38%) and benzotryptophan 35[18] (42%). NMR data of all the tryptophan derivatives (33-35) are in good agreement with previously reported data (Scheme 4).[18]

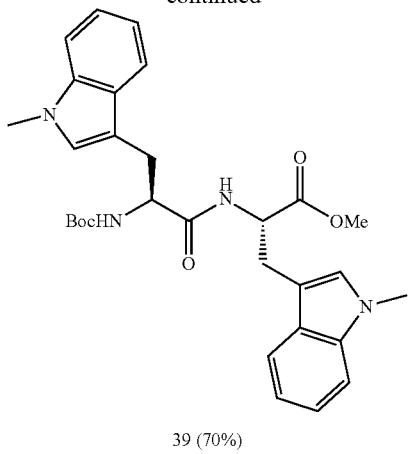

39 (70%)

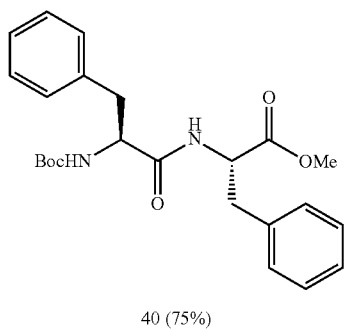

40 (75%)

Five dipeptides (36-40)[20-22] were prepared following an FBDD approach to combine the two potent Phe and Trp structural elements. Using DCC-HOBt coupling reaction of corresponding NBoc protected amino acids and methyl ester hydrochlorides in the presence of N-methylmorpholine (NMM) as the base, the desired dipeptides were obtained in good yields (Scheme 5).

Treatment of 41[23] with (±)-epibromohydrin in the presence of cesium carbonate as base afforded the 1:1 diastereomeric mixture of epoxy-tethered tryptophan 42. Deprotection of 42 by TFA(trifluoroacetic acid)-DCM afforded the trifluoroacetate salt 43 in 80% yield. Similarly, reaction with allyl bromide yielded 5-O-allyl tryptophan derivative 44 in 82% yield. Both the O-allyl group and the epoxy residue could serve as reactive handles for further derivatization (Scheme 6).

After deprotection of the tert-butyl carbamate of tryptophan derivatives by 4 N aq HCl in ethyl acetate, all of the free amines of the tryptophan derivatives were coupled with MTMSA (2) using PyBop as reagent and DIPEA as the base.[10] In each occasion, the corresponding MTMSA (2) analogues (45-63) were obtained in 10-26% yields (Scheme 7, vide SI for HPLC profile, HRMS data and individual yields of the reaction). The reaction of 43 with MTMSA (2) produced an inseparable mixture of diastereomeric MTMSA (2) coupled 1,2-diols, due to the opening of the epoxide ring under the reaction conditions.

To evaluate the anti-proliferative properties and selectivity of MTMSA (2) derivatives towards aberrant ETS transcription factors, such as EWS-FLI1, the following screening was performed: In the initial screen, MTM (1) analogues were tested for 72 h growth inhibition ($GI_{50}$) in TC-32 cells, a commonly Scheme 7. Synthesis of MTMSA (2) analogues

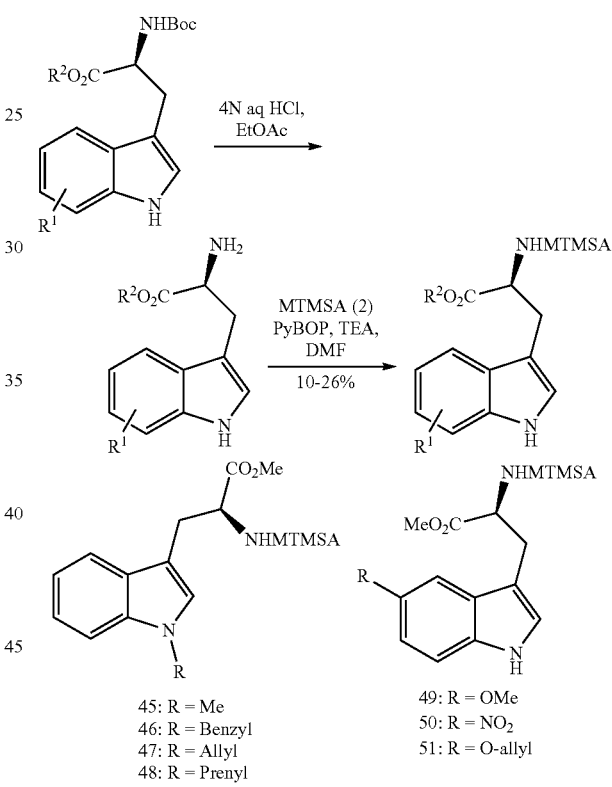

45: R = Me
46: R = Benzyl
47: R = Allyl
48: R = Prenyl

49: R = OMe
50: R = $NO_2$
51: R = O-allyl

Scheme 6. Alkylation of 5-hydroxy tryptophan

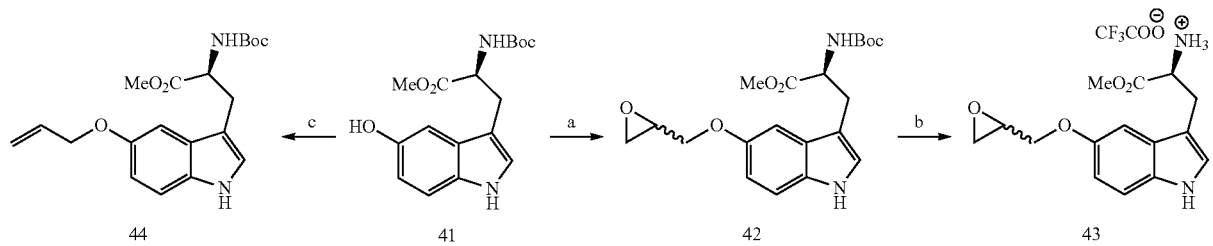

Reagents and conditions: a) $Cs_2CO_3$, DMF, (±)-Epibromohydrin, 80° C., 12 h, 68%; b) TFA, DCM, rt, 6 h, 80%; c) $Cs_2CO_3$, DMF, Allyl bromide, 80° C., 12 h, 82%.

-continued
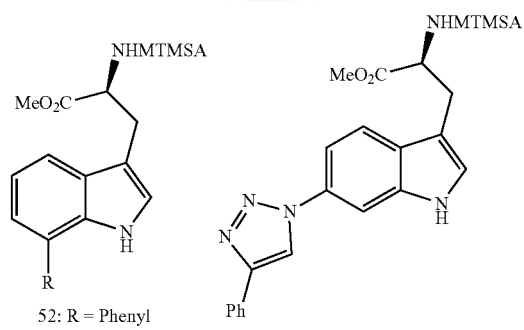
52: R = Phenyl
53: R = Allyl
54
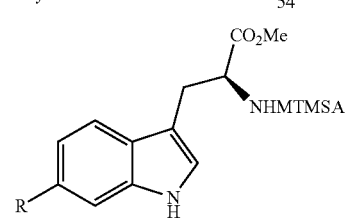
55: R = CF₃
56: R = F
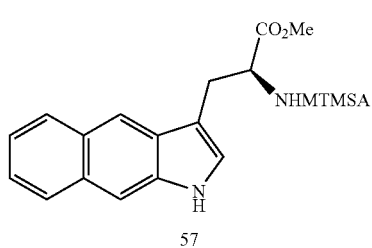
57
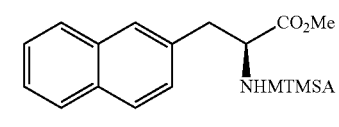
58
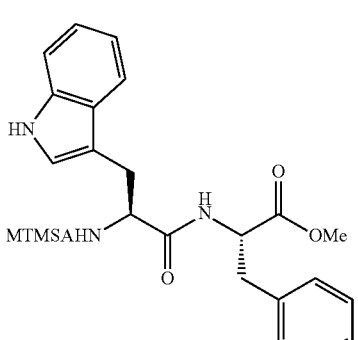
59
-continued
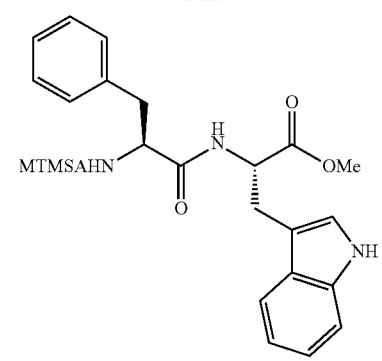
60
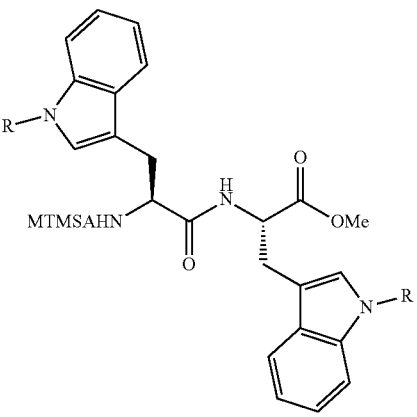
61: R = H
62: R = Me
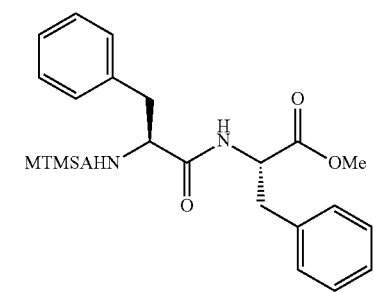
63

TABLE 1

Initial cytotoxicity ($GI_{50}$) screen in TC-32 (Ewing sarcoma) and PC-3 (non-Ewing sarcoma) cell line of MTMSA-Trp (3) analogues

| Entry | MTMSA (2) analogues | TC-32 Ewing sarcoma EWS-FLI1 Type 1 $GI_{50}$ (nM) | CI (95%) | PC-3 Prostate cancer No ETS Translocation $GI_{50}$ (nM) | CI (95%) | $GI_{50}$ ratio PC-3:TC-32 |
|---|---|---|---|---|---|---|
| 1 | 45, $R^1$ = Me, $R^2$ = $R^3$ = $R^4$ = H | 139 | 113-174 | 1557 | 1165-2252 | 11.2 |
| 2 | 46, $R^1$ = Bn, $R^2$ = $R^3$ = $R^4$ = H | 2297 | 1011-5884 | >10000 | NE* | NE* |
| 3 | 47, $R^1$ = Allyl, $R^2$ = $R^3$ = $R^4$ = H | 2715 | 1509-5216 | 3139 | 2553-9763 | 1.2 |
| 4 | 48a, $R^1$ = Prenyl, $R^2$ = $R^3$ = $R^4$ = H | >10000 | NE* | >10000 | NE* | NE* |
| 5 | 48b, $R^1$ = Prenyl, $R^2$ = $R^3$ = $R^4$ = H | >10000 | NE* | >10000 | NE* | NE* |
| 6 | 52, $R^2$ = Phenyl, $R^1$ = $R^3$ = $R^4$ = H | 2402 | 2160-2652 | >10000 | NE* | NE* |
| 7 | 53, $R^2$ = Allyl, $R^1$ = $R^3$ = $R^4$ = H | 794 | 535-1201 | 2989 | 2662-3687 | 3.8 |
| 8 | 54, $R^3$ = Trizolyl, $R^1$ = $R^2$ = $R^4$ = H | 1030 | 441-2496 | 5878 | >2652 | 5.7 |
| 9 | 55, $R^3$ = $CF_3$, $R^1$ = $R^2$ = $R^4$ = H | 2339 | 1958-3017 | 2395 | >2046 | 1.0 |
| 10 | 56, $R^3$ = F, $R^1$ = $R^2$ = $R^4$ = H | 27 | 25-30 | 187 | 145-242 | 6.9 |
| 11 | 49, $R^4$ = OMe, $R^1$ = $R^2$ = $R^3$ = H | 675 | 577-790 | 617 | 571-667 | 0.9 |
| 12 | 50, $R^4$ = $NO_2$, $R^1$ = $R^2$ = $R^3$ = H | 353 | 313-408 | 646 | 174-2051 | 1.8 |
| 13 | 51, $R^4$ = O-Allyl, $R^1$ = $R^2$ = $R^3$ = H | 53 | 37-75 | 454 | 275-763 | 8.6 |
| 14 | 57 | 3505 | 2974-5602 | >10000 | NE* | NE* |
| 15 | 58 | 541 | 353-834 | 1605 | 1106-2714 | 3.0 |
| 16 | MTMSA-Trp (3) | 16 | 13-20 | 76 | 66-88 | 4.8 |
| 17 | MTMSA-Phe (4) | 32 | 25-42 | 910 | 524-1606 | 28.4 |
| 18 | MTM (1) | 32 | 26-38 | 83 | 62-112 | 2.6 |
| 19 | MTMSA (2) | >10000 | NE* | >10000 | NE* | NE* |

*Regression not estimable used Ewing sarcoma cell line expressing EWS-FLI1 sensitive to MTM (1). Analogues with a $GI_{50}$<250 nM in the TC-32 cell line were then further tested against PC-3 cells, a prostate cancer cell line lacking EWS-FLI1 expression, also for 72 h growth inhibition (Table 1 and 2). In this assay, MTM (1) displayed 2.6-fold lower $GI_{50}$ in TC-32 cells as compared to PC-3 cells (Table 1). Thus, analogues with >3-fold selectivity towards TC-32 cell line were considered selective and were further investigated in a broader panel of cell lines to confirm and validate the selectivity in the context of multiple ETS fusion or aberrant ETS expression and across multiple cancer types that do not depend on the ETS fusions. In this secondary screen, analogues were tested in panel of seven additional Ewing sarcoma cell lines that express the majority of the EWS-ETS fusions and on the only available prostate cancer cell line (VCaP)

TABLE 2

Initial cytotoxicity (GI$_{50}$) screen against TC-32 (Ewing sarcoma) and
PC-3 (non-Ewing sarcoma) cell line of MTMSA (2)-dipeptide analogues

[Chemical structure of MTMSA (2)-dipeptide analogue]

| | | TC-32 Ewing sarcoma EWS-FLI1 Type 1 | | PC-3 Prostate cancer No ETS Translocation | | GI$_{50}$ ratio PC-3: |
|---|---|---|---|---|---|---|
| Entry | Analogues | GI$_{50}$ (nM) | CI (95%) | GI$_{50}$ (nM) | CI (95%) | TC-32 |
| 1 | 59, AA = Trp-Phe | 37 | 26-55 | 75 | 51-108 | 2.0 |
| 2 | 60, AA = Phe-Trp | 47 | 39-56 | 1128 | 578-2225 | 24.0 |
| 3 | 61, AA = Trp-Trp | 41 | 25-68 | 568 | 376-862 | 13.9 |
| 4 | 62, AA = NMeTrpNMeTrp | 7834 | NE* | >10000 | NE* | NE* |
| 5 | 63, AA = Phe-Phe | 232 | 121-448 | 1132 | 504-2586 | 4.9 |
| 6 | MTMSA-Trp (3) | 16 | 13-20 | 76 | 66-88 | 4.8 |
| 7 | MTMSA-Phe (4) | 32 | 25-42 | 910 | 524-1606 | 28.4 |
| 8 | MTM (1) | 32 | 26-38 | 83 | 62-112 | 2.6 |

Regression not estimable that expresses aberrant ERG. Results were compared to a panel of an additional 8 cancer cell lines that lack aberrant expression of ETS fusions (Table 3, FIG. 2) to identify the most desired analogue. MTM (1), MTMSA-Trp (3) and MTMSA-Phe (4) were used as controls.

Analogue 45 was designed to evaluate the potential role of the indole-NH. N-methylation will cut off the potential hydrogen-bonding donation and will increase the hydrophobicity of the indole ring. The N-methyl analogue 45 was found to be less active than MTMSA-Trp (3) against the TC-32 and PC-3 cell lines (Table 1; Entry 1), but more selective towards TC-32. The increasing hydrophobicity of 45 probably makes it more target-specific than MTMSA-Trp (3). Inspired by these results, N-benzylated analogue 46 was synthesized to evaluate the effect of an additional aromatic ring. Surprisingly, N-benzylated analogue 46 completely lost its activity, against both the TC-32 and the PC-3 cell lines, probably due to steric hindrance at the binding site (Table 1; Entry 2). Further modification by N-allylation (cf 47) and N-prenylation (cf 48a-b) to achieve a secondary interaction with the transcription factor also failed, resulting in complete loss of activity against both cell lines (Table 1; Entry 3, 4, and 5).

TABLE 3

Ewing sarcoma selectivity index of select MTMSA (2) analogues determined by median cytotoxicity (GI$_{50}$) in Ewing sarcoma cell lines compared to non-Ewing sarcoma cell lines

| Entry | MTMSA (2) Analogues | Median GI$_{50}$ in Ewing sarcoma cell lines (nM) | Median GI$_{50}$ in non-Ewing sarcoma cell lines (nM) | Ratio of Median GI$_{50}$ non-Ewing sarcoma:Ewing sarcoma (Selectivity Index) | Selectivity Index ratio Analogues:MTM (1) |
|---|---|---|---|---|---|
| 1 | 60 | 52 | 991 | 19.1 | 12.7 |
| 2 | 61 | 55 | 856 | 15.6 | 10.4 |
| 3 | 59 | 64 | 152 | 2.4 | 1.6 |
| 4 | 45 | 684 | 1644 | 2.4 | 1.6 |
| 5 | 51 | 485 | 532 | 1.1 | 0.7 |
| 6 | 56 | 466 | 419 | 0.9 | 0.6 |
| 7 | 63 | 561 | 1956 | 3.5 | 2.3 |
| 8 | MTM (1) | 46 | 71 | 1.5 | 1 |
| 9 | MTMSA-Phe (4) | 117 | 545 | 4.7 | 3.1 |
| 10 | MTMSA-Trp (3) | 47 | 109 | 2.3 | 1.5 |

Analogues 52 and 53 were synthesized to understand the steric requirement of the C7 position of the tryptophan ring. Both, the C7 phenyl analogue 52 and C7 allyl analogue 53 lost their activity, suggesting that the C7 position has to remain non-substituted to avoid steric hindrance (Table 1; Entry 6, 7). To explore a click chemistry handle and to add a more distant (from the indole) phenyl ring, the C6 functionalized analogue 54 was designed, but it was found to be inactive (Table 1; Entry 8), which discouraged further pursuit this approach for FBDD expansion.

It is well documented that incorporation of $CF_3$ or F in a drug molecule can strongly affect the binding affinity, pharmacokinetic properties, and bioavailability, mostly by inserting strong H-bond acceptor sites. The presence of a $CF_3$ or F substituent in a drug also increases the hydrophilicity and the electronic environment of the molecule, and significantly slows down the oxidative metabolism of the molecule without altering its size drastically. It was found that analogue 55 with C-6-$CF_3$ lost its activity completely in both cell lines (Table 1; Entry 9). However, the sterically less demanding C-6-F analogue 56 was found to be active in TC-32 cells with a selectivity of 6.9 and thus stood out as one of the potential candidates to be further studied and improved (Table 1; Entry 10). The increase in hydrophilicity while maintaining similar size as the unsubstituted tryptophan (cf 3) could be the reason behind its activity with improved selectivity, in comparison to 55. Electron rich or deficient tryptophans, 49 and 50, respectively, were both found to be less active than the parent MTMSA-Trp (3), suggesting the importance of the steric factors over the electronic nature of the tryptophan ring (Table 1; Entry 11 and 12). Incorporation of an allylic residue at indole-N (cf. 47) and C7 of the tryptophan ring (cf. 53) resulted in loss of activity in both the TC-32 and PC-3 cell lines, synthesized analogue 51 was synthesized with a 5-O-allyl tryptophan residue to explore substitution at the 5-position. Analogue 51 was found to be active in the TC-32 cell line with a selectivity of 8.6 (Table 1; Entry 13). These results indicate the accessibility of the C5 over the C7 position to incorporate an additional residue and to further expand the Trp residue by FBDD, with the ultimate goal to avail a secondary interaction with EWS-FLI1. Analogue 57, with an additional fused benzene ring added to tryptophan, documented a ~34 fold decrease in activity in the TC-32 cell line, once more restricting the steric requirements for interaction with EWS-FLI1, and thus wiped out the possibility of adding Π-donation directly to the tryptophan ring (Table 1; Entry 14). Similarly, analogue 58, where the indole ring was replaced by a naphthalene ring, lost activity in the TC-32 cell line, which again showed the importance of the indole ring for interactions with EWS-FLI1 (Table 1; Entry 15).

Dipeptide analogues 59-63 were tested in TC-32 cell lines to validate the FBDD concept in the most straightforward way, combining Phe and Trp. The fact that the N-methyl tryptophan analogue 45 showed a ~4 fold increase in selectivity (Table 1; Entry 1) impelled us to include Trp-N-methylation into this series of analogues. Analogue MTMSA-Trp-Phe (59) was found to have similar activity as MTMSA-Trp (3), but was less selective, while MTMSA-Phe-Trp (60), with the opposite arrangement of the amino acid residues, showed significantly increased selectivity compared to 3 (Table 2; Entry 1 and 2). Likewise, analogue MTMSA-Trp-Trp (61), which contains two consecutive tryptophan moieties, was found to have much better selectivity than MTMSA-Trp (3) (Table 2; Entry 3). Both 60 and 61 are about equally active in the TC-32 cell line (as 3). This shows the importance of the Trp residue to be in a more distant position from the DNA-interacting MTM (1) core, to interact with the transcription factor and thus may account for the observed improved selectivity towards the EWS-FLI1 expressing TC-32 cell line over the PC-3 cell line. It is noteworthy that the di-N-methyl analogue of 61 (cf 62) lost its activity completely, which indicates the importance of the beta indole-NH for the secondary interaction with EWS-FLI1 (Table 2; Entry 4). The loss of activity against TC-32 of analogue 63 indicates that a second phenylalanine residue is not advantageous (Table 2; Entry 5). These studies concluded that a tryptophan moiety in the more distant, second position of the analogues is crucial, and increases drastically the selectivity towards EWS-FLI1 while maintaining reasonable cytotoxic activity.

Figure 2:
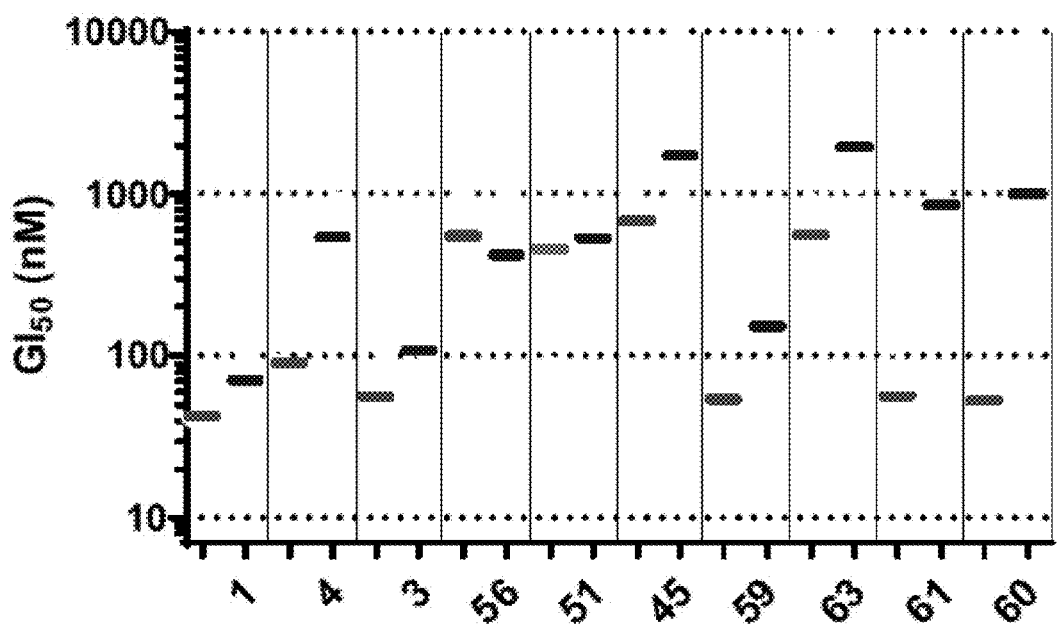
FIG. 2 includes data showing median $GI_{50}$ of select MTMSA (2) analogues in a panel of 8 Ewing sarcoma (TC-32, 5838, RD-ES, TC-71, A-673, ES-2, ES-7, ES-8) as well as 9 non-Ewing sarcoma (PC-3, DU 145, A549, LNCaP, U-118 MG, HeLa, HCT116, DMS 114, PANC-1) cell lines.

Overall, the above described initial screen identified 5 novel MTMSA (2) analogues with cytotoxicity ($GI_{50}$) in TC-32 cells of less than 250 nM, and selectivity against TC-32 cells greater than 3 times of that of PC-3, determined by PC-3:TC-32 $GI_{50}$ ratio (Table 1 and 2, highlighted in red). To deepen these findings and to further investigate the most promising analogues, the array of cancer cell lines was expanded to include a panel of 8 Ewing sarcoma cell lines (expressing aberrant ETS transcription factors) versus 9 non-Ewing sarcoma cell lines (lacking aberrant ETS transcription factors) (FIG. 2, vide SI).

Despite of initial lack in selectivity and cytotoxicity, analogues 59 and 63 were included, respectively, to get a complete overview of dipeptide analogues. MTM (1), MTMSA-Trp (3) and MTMSA-Phe (4) were used as controls. The final selectivity ratio was calculated by taking the median $GI_{50}$ of the non-Ewing sarcoma panel over the Ewing sarcoma panel (Table 3, FIG. 2). The median is presented. Of the 7 novel MTMSA (2) analogues that were tested on this secondary screen, only 3 were found to maintain selectivity greater than 3 against the panel of Ewing sarcoma cell lines versus non-Ewing sarcoma cell lines, namely 60, 61 and 63. The resulting Ewing sarcoma selectivity index ranked as follows: 60 (19.1)>61 (15.6) >>MTMSA-Phe (4) (4.7)>63 (3.5)>59 (2.4)=45 (2.4) >MTMSA-Trp (3) (2.3)>MTM (1) (1.5)>51 (1.1)>56 (0.9) (Table 3, FIG. 2).

Taking both Ewing sarcoma cytotoxicity ($GI_{50}$) and selectivity index into account, a potency order of MTMSA (2) analogues was determined to be 60>61>>MTMSA-Trp (3)=MTMSA-Phe (4)>MTM (1). Several initially promising MTMSA (2) analogues (cf 45, 51, 56, and 63) were eliminated in the secondary screen when tested against the panel of Ewing sarcoma cell lines because of their poor cytotoxicity ($GI_{50}$>250 nM). In contrast, analogue 59 was cytotoxic (median $GI_{50}$ of 64), but eliminated due to poor selectivity (selectivity index<3) (Table 3, FIG. 2). Interestingly and somewhat surprisingly, MTMSA-Phe (4) had a three times better ETS selectivity index of 4.7 than MTMSA-Trp (3, selectivity index 1.5), which initially was the lead molecule in this study (Table 3, FIG. 2). Based on these cytotoxicity screens, the overall best candidates for further development are analogues 60 and 61, with a median ETS cytotoxicity of ($GI_{50}$) 52 nM and 55 nM, respectively, and a drastically improved selectivity of >10-fold towards ETS depended cell lines, in comparison to MTM (1) (Table 3, FIG. 2).

Previous modification of MTM (1) leading to the identification of EC-8105 with improved suppression of EWS-FLI1 by almost 10-fold, focused on the introduction of an allyl carbonate residue in the 3B position of the disaccharide residue of MTM (1) (FIG. 1).[24] However, from the previous study of DNA-MTMSA-Trp (3) and DNA-MTMSA-Phe (4) crystal structures, it was anticipated that the 3-side chain can interact with FLI1 DNA binding domain.[12] Therefore, the identification of MTMSA-Phe-Trp (60) and MTMSA-Trp-Trp (61) with improved selectivity of 19.1 and 15.6, respectively, cemented the initial hypothesis that adding an additional tryptophan residue to MTMSA-Phe (4) and MTMSA-Trp (3) at the 3-side chain position would enhance their interaction with EWS-FLI1.

Additionally, all 7 MTMSA (2) analogues were tested in VCaP cells, which overexpress the TMPRSS2-ERG gene fusion, a common genomic alteration harbored by prostate cancer cells. It was initially expected that they would follow a similar selectivity trend to 5838 cells, which overexpress the more rare EWS-ERG gene alteration in Ewing sarcoma. The results indeed show that analogues 60 and 61 are the most selective for VCaP cells over other prostate cancer cell lines, with a selectivity ratio of 25.4 and 18.3, respectively (Table 4), consistent with their Ewing sarcoma selectivity index (cf Table 3, FIG. 2). Moreover, these analogues were more selective than MTM (1) for 5838 cells, however, not in the exact same rank order (Table 4).

Figure 3:
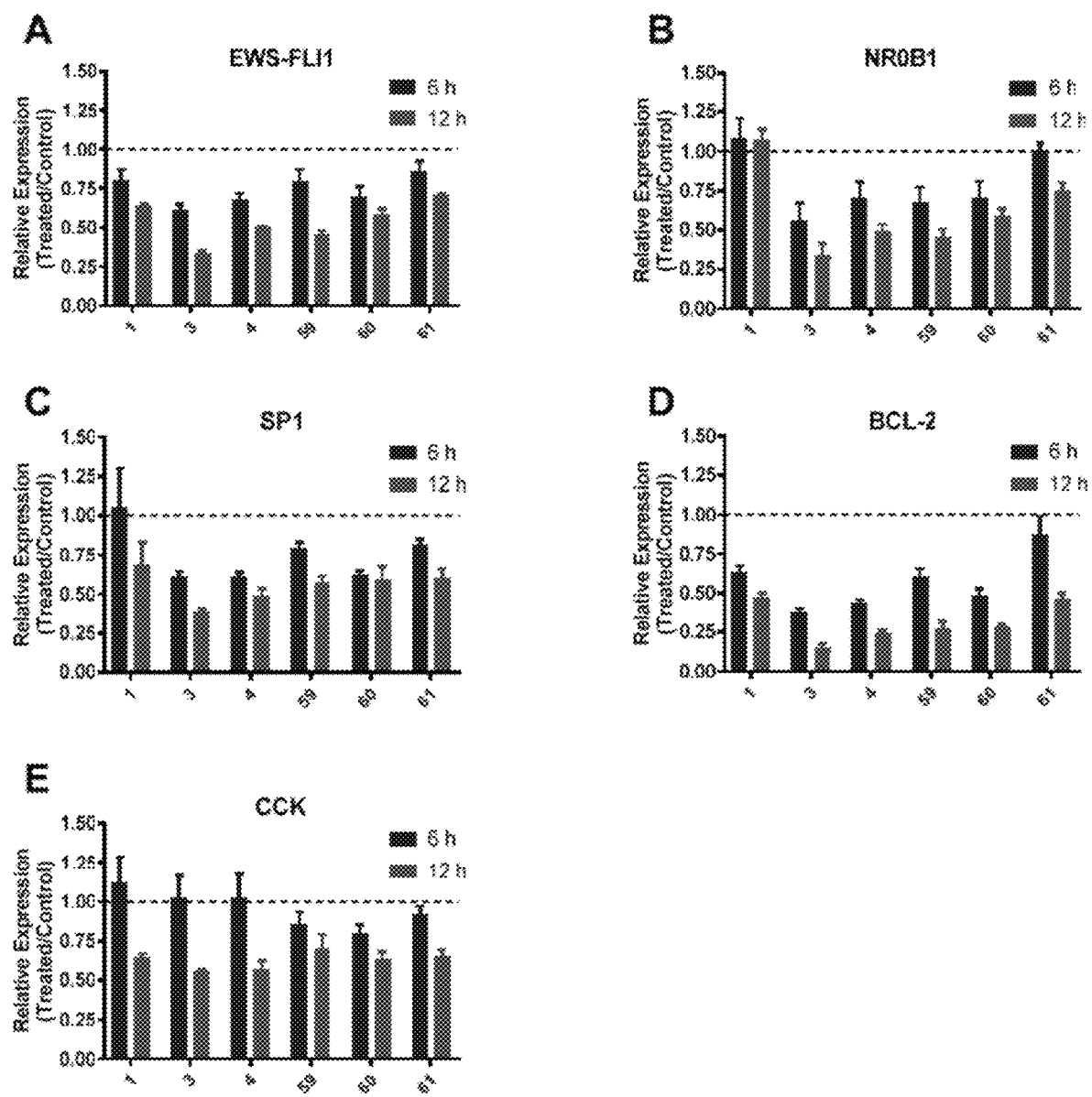
FIG. 3 displays mRNA expression of (A) EWS-FLI1 and associated gene, (B) NR0B1, are decreased after 6 and 12 h treatments with MTMSA analogues at respective $GI_{50}$, analyzed by qRT-PCR (quantitative reverse transcription polymerase chain reaction). mRNA expression of (C) Sp1, a well-known downstream target of MTM (1), and associated gene, (D) BCL-2 (B-cell lymphoma-2), were also analyzed. mRNA expression of (E) CCK (cholecystokinin) was analyzed as a negative control, previously reported as unaffected after 6 h of treatment with MTM at 100 nM.[26] Relative expressions were calculated using GAPDH expression.

CCK after 6 h treatment at the $GI_{50}$ (32 nM, ref. Table 1) for MTM (1), and minimal effect with MTMSA analogues. However, after 12 h, CCK mRNA expression is reduced to ~60% for both MTM (1) and MTMSA analogues (FIG. 3E).

Figure 4:
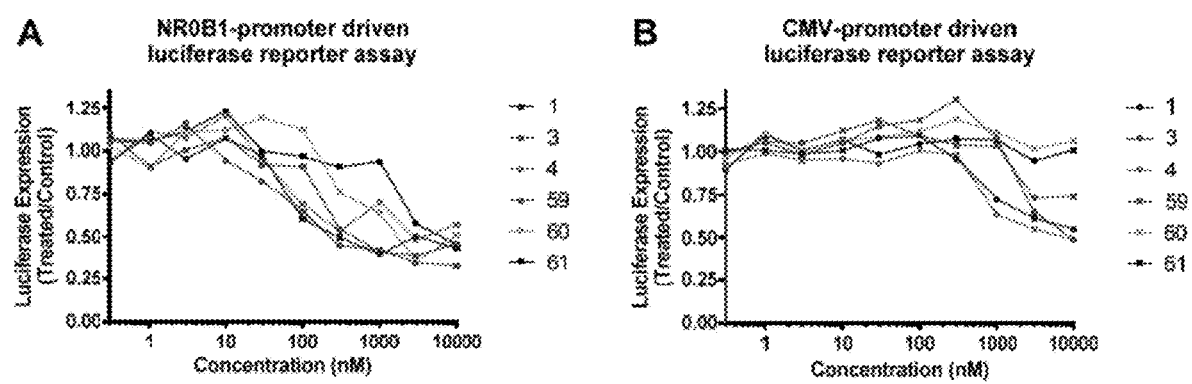
FIG. 4 displays (A) MTMSA analogues decrease the expression of luciferase controlled by NR0B1 (nuclear receptor subfamily 0, group B, member 1) promoter, a validated binding promoter of EWS-FLI1. TC-32 cells, expressing EWS-FLI1, were stably transfected with luciferase reporter vectors and treated for 12 h. (B) MTMSA analogues 60 and 61 did not decrease luciferase expression controlled by a non-specific CMV (Cytomegalovirus) promoter.

To further investigate the interference of MTM (1) and MTMSA analogues with the binding of ETS transcription factors, cell lines that express luciferase under the control of EWS-FLI1 were developed. TC-32 cells, which express EWS-FLI1, were stably transfected with a luciferase reporter vector and the control of the full length NR0B1 promoter. Cells were treated for 12 h with multiple concentrations between 0 and 10 μM. All MTMSA analogues decrease luciferase expression to 50% (FIG. 4A). Additionally, a luciferase reporter vector under the control of a CMV promoter was tested as a non-specific control. None of the analogues reduced CMV driven luciferase signal at the range of their $GI_{50}$ concentrations. MTM (1) and analogue 59 decrease CMV driven luciferase expression down to ~50% and ~75%, respectively, at concentrations between 1 and 10 μM, while analogues 60 and 61 had no effect at all, even when treated up to 10 μM (FIG. 4B).

TABLE 4

$GI_{50}$ and selectivity index of select MTMSA (2) analogues in cancer cells expressing aberrant ERG transcription factors.

| Entry | MTMSA (2) Analogues | VCaP Prostate Cancer TMPRSS2-ERG $GI_{50}$ (nM) | CI (95%) | Median $GI_{50}$ in prostate cell lines, lacking TMPRSS2-ERG | Ratio of median $GI_{50}$ Prostate cells lacking TMPRSS2-ERG: VCaP | 5838 Ewing Sarcoma EWS-ERG $GI_{50}$ (nM) | CI (95%) | Ratio of median $GI_{50}$ Non-Ewing sarcoma cell lines (cf Table 3): 5838 |
|---|---|---|---|---|---|---|---|---|
| 1 | 60 | 39 | 34-45 | 991 | 25.4 | 149 | 121-186 | 6.7 |
| 2 | 61 | 31 | 25-37 | 568 | 18.3 | 53 | 40-70 | 16.2 |
| 3 | 59 | 21 | 12-34 | 75 | 3.6 | 39 | 25-60 | 3.9 |
| 4 | 45 | 307 | 87-1430 | 1557 | 5.1 | 121 | 98-151 | 13.3 |
| 5 | 51 | 485 | 371-645 | 454 | 0.9 | 24 | 20-29 | 22.2 |
| 6 | 56 | 319 | 235-457 | 187 | 0.6 | 466 | 229-929 | 0.9 |
| 7 | 63 | 442 | 377-513 | 1132 | 2.6 | 579 | 350-966 | 3.4 |
| 8 | MTM (1) | 41 | 32-52 | 48 | 1.2 | 43 | 30-61 | 1.7 |
| 9 | MTMSA-Phe (4) | 150 | 70-321 | 732 | 4.9 | 38 | 30-49 | 14.3 |
| 10 | MTMSA-Trp (3) | 60 | 45-80 | 76 | 1.3 | 6 | 4-10 | 18.2 |

Since it is recognized that MTM displaces Sp1 from DNA and likely affects the expression of Sp1 target genes (e.g., BCL-2), qRT-PCR was performed to determine the effect of MTM (1) and MTMSA analogue treatment on the expression of those genes as well as on EWS-FLI1 and its target gene NR0B1. The expression of EWS-FLI1 was reduced to approximately 70-75% after 6 h and then further reduced after 12 h treatment (FIG. 3A). The NR0B1 promoter contains a microsatellite region of GGAA repeats of DNA that binds to EWS-FLI1 for transcriptional regulation, through the conserved ETS binding domain of FLI1.[25] NR0B1 mRNA expression was not affected by MTM (1) at the $GI_{50}$ at 6 and 12 h, but was reduced to ~75% after 6 h of treatment with MTMSA analogues, and it was further reduced after 12 h (FIG. 3B). In contrast both Sp1 and BCL-2 mRNA expression was reduced with MTM (1) and MTMSA analogues treatments after 6 and 12 h (FIGS. 3C and 3D). Previously it was reported that 6 h treatment with 100 nM MTM (1) had no effect on mRNA expression of CCK.[26] Therefore, this gene was used as a negative control. The results also showed no change in mRNA expression of Lack of effect of analogue MTMSA-Phe-Trp (60) and MTMSA-Trp-Trp (61) on CMV promoter driven transcription while maintaining activities against EWS-FLI1 mediated transcription support the observed selectivity in the cytotoxicity assays (cf. Table 3, FIG. 2). Furthermore, MTMSA-Trp-Phe (59), which reduces CMV promoter driven transcription, lacks selectivity in the cytotoxicity assays (cf. Table 3, FIG. 2). This supports the conclusions made after the initial screening (Table 2), namely that a Trp residue in a second, more distant position from the MTM (1)-DNA binding core, is crucial for an interaction with the EWS-FLI1 transcription factor. The importance of the Phe or the Trp moiety in the first position of the MTMSA-3-side chain and the impact of an additional Trp residue (cf MTMSA (2) tripeptide analogues) remains to be investigated.

CONCLUSIONS

This study was aimed on refinement of two amino acid derivatives of MTMSA (2), namely, MTMSA-Trp (3) and MTMSA-Phe (4), which both showed promising activity and increased selectivity in a preliminary cytotoxicity assay looking at effects on cell lines overexpressing aberrant ETS transcription factors. This was expected, since crystallographic studies investigating DNA-FLI1 interactions and the DNA binding modalities of the MTMSA-Phe (4) and MTMSA-Trp (3) analogues resulted in a new mode-of-action hypothesis of MTM (1) and these derivatives: a ternary complex of MTM (1)-DNA-FLI1 (similarly MTM (1)-DNA-ERG in the context of prostate cancer), in which the MTM (1) analogue binds to the minor groove of certain DNA microsatellites, with its core and trisaccharide side chain, and simultaneously to the FLI1 portion of EWS-FLI1 within the major groove of DNA. Aromatic residues of MTMSA (2) analogues are well poised to increase protein binding. Initially, the focus was on refining the Trp residue, since MTMSA-Trp (3) showed better cytotoxicity than MTMSA-Phe (4) (Table 3). The array of MTMSA-Trp (3) derivatives was achieved through iridium-catalyzed borylation and palladium catalyzed tryptophan syntheses. The borylated tryptophans were further used to diversify the indol ring of tryptophan, before the PyBop coupling reaction with MTMSA (2) to generate sterically and electronically different MTMSA-Trp (3) analogues.

Later, the studies were expanded to a fragment based drug development (FBDD) approach, to combine the protein interactive aromatic rings of Trp and Phe, which both appeared to be advantageous elements to increase selectivity towards ETS fusion expressing cell lines. These studies started with phenyl-expanded Trp derivatives, in which the indole of Trp was expanded by an aromatic ring, or through phenyl-Trp derivatives, and ended with dipeptide analogues of MTMSA (2), with all combinations of dipeptide side chains, namely MTMSA-Trp-Phe (59), MTMSA-Phe-Trp (60), MTMSA-Phe-Phe (63) and MTMSA-Trp-Trp (61).

Initially all analogues were tested in the Ewing sarcoma TC-32 cell line that expresses EWS-FLI1 type I, the genotype in the majority of Ewing sarcoma patients. For target specificity analysis, these analogues were also tested in prostate PC-3 cell line that lacks dependence on aberrant ETS transcription factors. These comparative tests resulted in the identification of 7 MTMSA analogues with increased specificity towards the Ewing sarcoma cell line (Table 1 and 2). As a result they were further evaluated against multiple Ewing sarcoma cell lines, as well as VCaP prostate cancer cell line, all of whom express various aberrant ETS transcription factors. This was compared to a panel of cell lines lacking expression of aberrant ETS transcription factors. Analogues 60 and 61 were found to have cytotoxic activities comparable to MTM (1), but showed >10-fold increased selectivity towards aberrant ETS dependent cell lines (Table 3 and 4, FIG. 2). To further investigate if this selectivity is a result of activity against aberrant ETS transcription factors the effects on EWS-FLI1 and target gene NR0B1 mRNA expression with analogue treatment were considered. Furthermore, a luciferase reporter vector controlled by NR0B1 promoter, which binds to EWS-FLI1, was tested. Analogues 60 and 61 were found to decreased EWS-FLI1 and NR0B1 mRNA expression, as well as NR0B1 promoter driven luciferase signal (FIGS. 3A and 3B, FIG. 4A). However, analogue 60 and 61 did not decrease non-specific CMV promoter driven luciferase signal (FIG. 4B), correlating well with the observed selectivity in cytotoxicity assays (Table 3, FIG. 2). This is in comparison to MTM (1) and analogue 59, which decreased non-specific CMV promoter driven luciferase signal (FIG. 4B), and therefore had no observed selectivity in cytotoxicity assays (Table 3, FIG. 2).

This expanded study confirmed that the tryptophan ring in second position of the 3-side chains of analogue 60 and 61 may play a useful role to afford better selectivity against ETS dependent cell lines.

Experimental Section

Chemistry

All commercial reagents were used without further purification. The required amine for the synthesis of 56 and 58 were prepared by protecting the commercially available corresponding tryptophan in the presence of thionyl chloride in methanol. Solvents were dried and distilled following the standard procedures. TLC was carried out on pre-coated plates (Merck silica gel 60, GF254), and the spots were visualized with UV, fluorescent light or by charring with phosphomolybdic acid hydrate (PMA). Column chromatography was performed on silica gel (230-400 mesh). $^1$H and $^{13}$C NMR spectra for the compounds were recorded with Varian 400 or 600 MHz spectrometers. $^1$H and $^{13}$C chemical shifts are reported in ppm downfield of tetramethylsilane and referenced to residual solvent peaks (CHCl$_3$; $\delta_H$=7.26 and $\delta_C$=77.23, d$_4$-MeOH; $\delta_H$=3.31 and $\delta_C$=49.1). Multiplicities are reported using the following abbreviations: s=singlet, d=doublet, t=triplet, q=quartet, m=multiplet, br=broad resonance, ap=apparent. The phrase 'usual work up' or 'worked up in usual manner' refers to washing of the organic phase with water (2×¼ the volume of organic phase) and brine (1×¼ the volume of organic phase), and drying (anhydrous Na$_2$SO$_4$), filtration, and concentration under reduced pressure. Yields referred to isolated yields after purification. Analytical LC/MS was performed on a Waters 2965 (Kinetex 5U EVO C18 100A, 250×4.6 mm, a linear gradient from A/B 75:25 to 30:70 (20 min), 30:70 to 0:100 (2 min), 0:100 (2 min,); 0:100 to 75:25 (2 min), 75:25 (4 min) (A=H$_2$O+0.1% formic acid, B=MeCN+0.1% formic acid), flow rate 0.5 mL/min) equipped with an Waters ZQ 2000 mass spectrometer and Waters 2996 photodiode array detector. The purity of all analogues used in the bioassays was determined by this method to be >95%. Mass spectra were taken on ABSciex QTOF mass spectrometer.

General Procedure A: N-alkylation of 6

To a stirred solution of 6 (1 equiv) in dry DMF was added 60% NaH (1.5 equiv) in portion at 0° C. and stirred for 30 min after which respective halide (1.5 equiv) was added. The reaction mixture was stirred at rt for 12 h, cooled to 0° C. and quenched with methanol. It was diluted with ethyl acetate, worked up in usual manner, and subjected to column chromatography with silica gel using 20% ethyl acetate in hexane as eluent.

General Procedure for the Deprotection of Phthalimide

To a stirred solution of phtalimide (cf. 7 to 10) (1 equiv) in MeOH-DCM (1:1; 10 mL) was added hydrazine hydrate (1.5 equiv) and the reaction mixture was stirred at rt for 24 h. It was then filtered through celite, washed with ethyl acetate and concentrated under reduced vacuum. It was purified in reverse phase silica using 20% acetonitrile in water as mobile phase to obtain the free amine (cf. 11 to 14) in 45-60% yield. The free amine was only characterized by LCMS and directly used without further purification in the PyBop coupling reaction with MTMSA (2).

General Procedure B: Procedure of Synthesis of Tryptophan from Aldehyde 28

A mixture of o-iodoaniline (1.1 equiv), aldehyde 28 (1.0 equiv), and DABCO (3 equiv) in dry DMF was degassed for 30 min using argon. Pd(OAc)$_2$ (5 mol %) was added to the reaction, and the resulting reaction mixture was heated at 85° C. in a pressure tube for 24 h. The reaction mixture was cooled to room temperature, diluted with water, extracted with ethyl acetate and worked up in usual manner. The crude product was purified by flash column chromatography to obtain the corresponding tryptophan derivative.

General Procedure C: Procedure for HOBt-DCC Coupling Reaction[20]

To a solution of NBocAA-OH (1 equiv) in dry THF were added HOBt (hydroxybenzotriazole) (1.2 equiv) and DCC (N,N'-dicycliohexylcarbodiimide) (1.2 equiv) and stirred at 0° C. for 1 h. Then HCl.AA-OMe (1.1 equiv) was added to the reaction mixture and pH was adjusted in between 8-9 by adding excess NMM. The reaction mixture was stirred for 12 h at room temperature, filtered and concentrated under reduced pressure. The residue was dissolved in ethyl acetate, washed with saturated aq NaHCO$_3$ and worked up in usual manner. The crude product was purified by flash column chromatography to obtain the corresponding protected dipeptide.

General Procedure D: Procedure for PyBop Coupling Reaction

To a stirred solution of MTMSA (2) (1 equiv) in dry DMF were added PyBop (1.5 equiv), free amine (3.0 equiv) and excess triethyl amine (adjusted to pH 8). The reaction mixture was stirred at room temperature under argon atmosphere until disappearance of MTMSA (2). It was quenched by adding saturated NaCl solution and extracted with n-BuOH. The organic fraction was collected and concentrated under reduced pressure and purified by HPLC to obtain pure MTMSA (2) analogues.

Methyl (S)-3-(1-benzyl-1H-indol-3-yl)-2-(1,3-dioxoisoindolin-2-yl)propanoate (8)

Compound 8 (512 mg, 70%) was prepared as a yellow semisolid by N-benzylation of 6 (581 mg, 1.67 mmol) with benzyl bromide (0.3 ml, 2.5 mmol) using 60% NaH (100 mg, 2.5 mmol) as base, following the general procedure A. $^1$H NMR (400 MHz, CDCl$_3$) δ 7.75-7.73 (m, 2H), 7.67-7.62 (m, 3H), 7.17-7.05 (m, 6H), 6.93 (s, 1H), 6.89-6.86 (m, 2H), 5.30 (dd, J=9.9, 6.4 Hz, 1H), 5.16 (ABq, J=14.8 Hz, 2H), 3.81 (s, 3H), 3.79-3.75 (m, 2H).; $^{13}$C NMR (100 MHz, CDCl$_3$) δ 169.8, 167.6, 137.6, 136.6, 134.1, 131.8, 128.7, 128.0, 127.5, 127.0, 126.6, 123.5, 122.1, 119.5, 118.9, 110.3, 109.8, 53.0, 52.8, 49.9, 24.9.; HRMS (TOF MS ES+) m/z calcd for C$_{27}$H$_{23}$N$_2$O$_4$ [M+H]$^+$ 439.1659, found 439.1638.

Methyl (S)-3-(1-allyl-1H-indol-3-yl)-2-(1,3-dioxoisoindolin-2-yl)propanoate (9)

Compound 9 (400 mg, 85%) was prepared as a yellow semisolid by N-allylation of 6 (425 mg, 1.22 mmol) with allyl bromide (0.16 ml, 1.83 mmol) using 60% NaH (75 mg, 1.83 mmol) as base, following the general procedure A. $^1$H NMR (400 MHz, CDCl$_3$) δ 7.76-7.73 (m, 2H), 7.66-7.60 (m, 2H), 7.61 (d, J=7.9 Hz, 1H), 7.19 (d, J=8.4 Hz, 1H), 7.13 (t, J=8.0, 1H), 7.05 (t, J=8.4, 1H), 6.88 (s, 1H), 5.83-5.74 (m, 1H), 5.27 (t, J=7.6 Hz, 1H), 4.97-4.93 (m, 1H), 4.78-4.73 (m, 1H), 4.62-4.50 (m, 2H), 3.80 (s, 3H), 3.75 (d, J=8.1 Hz, 2H).; $^{13}$C NMR (100 MHz, CDCl$_3$) δ 169.8, 167.6, 136.4, 134.1, 133.5, 131.9, 127.9, 126.6, 123.5, 121.9, 119.3, 118.8, 116.7, 110.1, 109.7, 53.0, 52.8, 48.5, 24.9.; HRMS (TOF MS ES+) m/z calcd for C$_{23}$H$_{21}$N$_2$O$_4$ [M+H]$^+$ 389.1501, found 389.1488.

Methyl (R)-2-(tert-butoxycarbonyl)-3-(7-iodo-1H-indol-3-yl)propanoate (18)

To a solution of 15 (740 mg, 1.67 mmol) in methanol (15 mL) in a pressure tube, were added CuI (35 mg, 0.183 mmol, 10.0 mol %), 1,10-phen (60.0 mg, 0.34 mmol, 20.0 mol %) and KI (420 mg, 2.53 mmol, 1.50 equiv). The mixture was stirred at room temperature, water (3.5 mL) was added and it was sealed under air. The mixture was heated at 80° C. for 2 h, cooled to room temperature and diluted with water (40 ml). It was extracted with Et$_2$O (3×35 mL) and worked up in usual manner. The crude compound was subjected to column chromatography with silica gel using 30% ethyl acetate in hexane as eluent to obtain 18 as a white solid. $^1$H NMR (400 MHz, CDCl$_3$) δ 8.19 (s, 1H), 7.54 (apt, J=8.4 Hz, 2H), 7.06 (s, 1H), 6.88 (t, J=7.7 Hz, 1H), 5.08 (d, J=8.2 Hz, 1H), 4.64 (dd, J=12.8, 6.0 Hz, 1H), 3.67 (s, 3H), 3.30-3.20 (m, 2H), 1.42 (s, 9H).; $^{13}$C NMR (100 MHz, CDCl$_3$) δ 172.7, 155.3, 138.1, 131.0, 128.0, 123.3, 121.5, 119.1, 112.1, 80.1, 76.1, 54.3, 52.5, 28.52, 28.49.; HRMS (TOF MS ES+) m/z calcd for C$_{17}$H$_{22}$IN$_2$O$_4$ [M+H]$^+$445.0625, found 445.0620.

Methyl (R)-3-(7-allyl-1H-indol-3-yl)-2-(tert-butoxycarbonyl)propanoate (17)

To a stirred solution of 18 (115 mg, 0.29 mmol) in dry toluene (5 ml), were added allyl tributyltin (0.13 ml, 0.4 mmol) and tetrakis(triphenylphosphine)palladium(0) (70 mg, 0.06 mmol, 20 mol %). The reaction mixture was refluxed under argon atmosphere for 24 h, cooled to room temperature and diluted with ethyl acetate (50 ml). After usual work up followed by column chromatography with silica gel using 25% ethyl acetate in hexane as eluent obtained 17 (56 mg, 60%) as a yellow liquid. $^1$H NMR (400 MHz, CDCl$_3$) δ 8.17 (s, 1H), 7.44 (d, J=7.8 Hz, 1H), 7.07 (t, J=7.5 Hz, 1H), 7.03-6.97 (m, 2H), 6.11-6.01 (m, 1H), 5.28-5.13 (m, 2H), 5.07 (d, J=8.2 Hz, 1H), 4.64 (q, J=6.3 Hz, 1H), 3.68 (s, 3H), 3.62 (d, J=6.5 Hz, 2H), 3.28 (dd, J=5.6, 2.6 Hz, 2H), 1.42 (s, 9H).; $^{13}$C NMR (100 MHz, CDCl$_3$) δ 173.0, 155.4, 136.9, 135.7, 122.7, 122.5, 122.3, 120.1, 117.4, 116.6, 110.7, 80.0, 54.4, 52.4, 37.0, 28.5, 28.2.; HRMS (TOF MS ES+) m/z calcd for C$_{20}$H$_{27}$N$_2$O$_4$ [M+H]$^+$ 359.1971, found 359.1965.

Methyl (R)-2-(tert-butoxycarbonyl)-3-(7-phenyl-1H-indol-3-yl)propanoate (20)

To a stirred solution of 18 (160 mg, 0.36 mmol) in dry toluene (5 ml), were added iodobenzene (70 μL, 0.6 mmol), K$_3$PO$_4$ (180 mg, 0.84 mmol), Sphos (18 mg, 0.044 mmol, 12 mol %), and tris(dibenzylideneacetone)dipalladium(0) (20 mg, 0.02 mmol, 5 mol %). The reaction mixture was heated under argon atmosphere at 80° C. for 16 h, cooled to room temperature and diluted with ethyl acetate (50 ml). Work up in usual manner followed by column chromatography with silica gel using 20% ethyl acetate in hexane as eluent obtained 17 (100 mg, 70%) as a yellow liquid. $^1$H NMR (400 MHz, CDCl$_3$) δ 8.34 (s, 1H), 7.62 (d, J=7.2 Hz, 2H), 7.56-7.48 (m, 3H), 7.39 (t, J=7.2 Hz, 1H), 7.22-7.19 (m, 2H), 7.02 (s, 1H), 5.11 (d, J=8.2 Hz, 1H), 4.66 (q, J=6.0 Hz, 1H), 3.70 (s, 3H), 3.37-3.27 (m, 2H), 1.44 (s, 9H).; $^{13}$C NMR (100 MHz, CDCl$_3$) δ 172.9, 155.4, 139.2, 134.2, 129.3, 128.4, 128.3 127.7, 125.9, 123.2, 122.3, 120.4, 118.3, 110.9, 80.0, 54.4, 52.5, 28.5, 28.3.; HRMS (TOF MS ES+) m/z calcd for C$_{25}$H$_{26}$N$_2$O$_4$ [M+H]$^+$ 395.1971, found 395.1965.

Methyl (R)-3-(6-azido-1-(triisopropylsilyl)-1H-indol-3-yl)-2-(tert-butoxycarbonyl)propanoate (24, mixture of C6 and C5 isomers, major C6 isomer)

To a solution of 22 (244 mg, 0.41 mmol) in methanol (5 ml), were added sodium azide (40 mg, 0.61 mmol) and copper(II)acetate monohydrate (8.2 mg, 0.041 mmol, 10 mol %). The reaction mixture was heated at 55° C. under air for 12 h, diluted with ethyl acetate and worked up in usual manner. Purification by column chromatography with silica gel using 25% ethyl acetate in hexane as eluent obtained 24 (147 mg, 70%) as a yellow liquid as an inseparable mixture of two isomers. $^1$H NMR (400 MHz, CDCl$_3$, Major C6-azido isomer) δ 7.49 (d, J=8.5 Hz, 1H), 7.08 (d, J=1.9 Hz, 1H), 7.00 (s, 1H), 6.86 (dd, J=8.5, 1.9 Hz, 1H), 5.09 (d, J=8.2 Hz, 1H), 4.64 (q, J=5.6 Hz, 1H), 3.63 (s, 3H), 3.26-3.22 (m, 2H), 1.68-161 (m, 3H), 1.43 (s, 9H), 1.13 (d, J=6.0 Hz, 18H).; HRMS (TOF MS ES+) m/z calcd for C$_{26}$H$_{42}$N$_5$O$_4$Si [M+H]$^+$ 516.3006, found 516.3001.

Methyl (2R)-2-(tert-butoxycarbonyl)-3-(6-(4-phenyl-1H-1,2,3-triazol-1-yl)-(triisopropylsilyl)-1H-indol-3-yl)propanoate (25, mixture of C6 and C5 isomers, major C6 isomer)

To a solution of 24 (150 mg, 0.3 mmol) in dry DCM (2 mL), were added phenyl acetylene (32 μL, 0.28 mmol), copper(I) iodide (1.2 mg, 0.02 equiv), DIPEA (0.04 equiv), and acetic acid (1 μL, 0.06 equiv). The reaction mixture was stirred at room temperature for 2 h, diluted with DCM (3 mL) and purified by column chromatography with silica gel using 30% ethyl acetate in hexane as eluent obtained 25 (130 mg, 72%) as a yellow liquid as an inseparable mixture of two isomers. $^1$H NMR (400 MHz, CDCl$_3$, major C6 isomer) δ 8.20 (s, 1H), 8.01 (d, J=1.8 Hz, 1H), 7.95-7.91 (m, 2H), 7.63 (d, J=8.5 Hz, 1H), 7.47-7.39 (m, 3H), 7.37-7.30 (m, 1H), 7.14 (s, 1H), 5.13 (d, J=8.4 Hz, 1H), 4.67 (q, J=6.3 Hz, 1H), 3.63 (s, 3H), 3.29 (apt, J=6.2 Hz, 2H), 1.73-166 (m, 3H), 1.43 (s, 9H), 1.14 (d, J=7.5 Hz, 18H).; HRMS (TOF MS ES+) m/z calcd for C$_{34}$H$_{48}$N$_5$O$_4$Si [M+H]$^+$ 618.3476, found 618.3447.

Methyl 2-tert-butoxycarbonylamino-3-(6-trifluoromethyl-1-triisopropylsilanyl-1H-indol-3-yl)propanoate (26)

A mixture of 22 (150 mg, 0.25 mmol), 1,10-Phen (9 mg, 0.05 mmol), LiOH.H$_2$O (21 mg, 0.5 mmol) CuTC (5 mg, 0.025 mmol) and 3,3-Dimethyl-1-(trifluoromethyl)-1,2-benziodoxol (Togni's reagent) (91 mg, 0.28 mmol) in DCM (2 mL) were stirred under argon atmosphere at rt for 12 h. The reaction mixture was diluted with DCM (10 mL), filtered through a cilite pad and concentrated under reduced pressure. The crude compound was purified by column chromatography with silica gel using 30% ethyl acetate in hexane as eluent obtained 26 (58 mg, 60%) as a yellow liquid as an inseparable mixture of two isomers. $^1$H NMR (400 MHz, CDCl$_3$, Mixture of C5 and C6 isomers) δ 7.77 (d, J=1.3 Hz), 7.70 (s), 7.59 (d, J=8.4 Hz), 7.35 (dd, J=14.3, 8.4 Hz), 7.27 (d, J=10.8 Hz), 7.15 (s), 6.93 (s), 5.05 (t, J=8.6 Hz), 4.63 (dq, J=13.5, 5.9 Hz), 3.61 (s), 3.27-3.05 (m), 1.71-1.56 (m), 1.42 (s), 1.21-1.06 (m). $^{19}$F NMR (376 MHz, CDCl$_3$, Mixture of C5 and C6 isomers) δ−54.2, −60.5. HRMS (TOF MS ES+) m/z calcd for C$_{18}$H$_{22}$F$_3$N$_2$O$_4$ [M+H]$^+$386.1453, found 386.1462.

Methyl 2-[2-tert-butoxycarbonylamino-3-(1-methyl-1H-indol-3-yl)-propionylamino]-3-(1-methyl-1H-indol-3-yl)propanoate (39)

Compound 39 (58 g, 70%) was prepared following the general procedure A by HOBt-DCC coupling of BocNH-NMeTrp-OH (50 mg, 0.15 mmol) with NH$_2$-NMeTrp-OMe (40 mg, 0.17 mmol) in the presence of HOBt (20 mg, 0.15 mmol) and DCC (35 mg, 0.17 mmol) in THF (5 ml) as a white solid. Mp: 128° C.; $^1$H NMR (400 MHz, CDCl$_3$) δ 7.66 (d, J=7.9 Hz, 1H), 7.29 (d, J=8.1 Hz, 1H), 7.27-7.23 (m, 1H), 7.23-7.18 (m, 1H), 7.14 (t, J=7.0 Hz, 3H), 6.94 (s, 1H), 6.85 (t, J=7.3 Hz, 1H), 6.38-6.26 (m, 2H), 5.09 (d, J=8.1 Hz, 1H), 4.79 (q, J=6.0 Hz, 1H), 4.45 (d, J=7.5 Hz, 1H), 3.67 (s, 3H), 3.59 (s, 3H), 3.55 (s, 3H), 3.36 (q, J=4.7 Hz, 1H), 3.15 (td, J=13.8, 12.8, 6.3 Hz, 2H), 3.06 (dd, J=14.7, 5.4 Hz, 1H), 1.38 (s, 9H).; $^{13}$C NMR (100 MHz, CDCl$_3$) δ 171.6, 171.1, 155.3, 136.9, 136.7, 128.2, 128.0, 127.7, 125.7, 121.8, 121.7, 119.3, 119.1, 119.0, 118.3, 109.3, 108.9, 107.8, 52.8, 52.2, 32.6, 32.5, 28.2, 28.1, 27.5. HRMS (TOF MS ES+) m/z calcd for C$_{30}$H$_{37}$N$_4$O$_5$ [M+H]$^+$ 533.2764, found 533.2835.

Methyl 2-(2-tert-butoxycarbonylamino-3-phenyl-propionylamino)-3-phenylpropanoate (40)

Compound 40 (1.8 g, 75%)) was prepared following the general procedure A by HOBt-DCC coupling of BocNH-Phe-OH (2.0 g, 5.65 mmol) with HCl.NH$_2$-Phe-OMe (1.12, 6.21 mmol) in the presence of HOBt (900 mg, 6.67 mmol) and DCC (1.38 g, 6.67 mmol) in THF (60 ml) as a white solid. Mp: 117° C.; $^1$H NMR (400 MHz, CDCl$_3$) δ 7.29-7.26 (m, 1H), 7.24 (td, J=3.8, 1.4 Hz, 2H), 7.21 (dt, J=5.8, 1.6 Hz, 3H), 7.17 (d, J=7.4 Hz, 2H), 6.95 (dd, J=6.4, 2.3 Hz, 2H), 6.24 (br s, 1H), 4.91 (br s, 1H), 4.76 (d, J=6.7 Hz, 1H), 4.31 (br s, 1H), 3.65 (s, 3H), 3.06-2.95 (m, 4H), 1.38 (s, 9H).; $^{13}$C NMR (100 MHz, CDCl$_3$) δ 171.3, 170.7, 155.2 136.5, 135.6, 129.3(3C), 129.2(2C), 128.6, 128.5(2C), 127.1, 126.9, 53.2, 52.3(2C), 37.9(2C), 28.2(3C).; HRMS (TOF MS ES+) m/z calcd for C$_{24}$H$_{30}$N$_2$NaO$_5$ [M+Na]$^+$449.2052, found 449.2027.

Methyl 2-tert-butoxycarbonylamino-3-(5-oxiranylmethoxy-1H-indol-3-yl)propanoate (42)

To a stirred solution of 41 (200 mg, 0.60 mmol) in dry DMF (6 mL) were added cesium carbonate (390 mg, 1.2 mmol) and (±)-epibromohydrin (77 μL, 0.90 mmol). The reaction mixture was stirred at 60° C. for 12 h, cooled to rt and concentrated under reduced pressure. It was diluted with ethyl acetate and worked up in usual manner and subjected to column chromatography with silica gel using 30% ethyl acetate in hexane as eluent to afford 42 (150 mg, 68%, dr=1:1) as a yellow semi solid. $^1$H NMR (400 MHz, CDCl$_3$) δ 8.40 (s, 1H), 7.20 (d, J=8.7 Hz, 1H), 7.02 (d, J=2.4 Hz, 1H), 6.94 (s, 1H), 6.86 (dd, J=8.8, 2.4 Hz, 1H), 5.13 (dt, J=6.7, 3.4 Hz, 1H), 4.61 (dt, J=14.7, 5.9 Hz, 1H), 4.25 (dt, J=11.0, 3.3 Hz, 1H), 3.99 (dt, J=10.7, 5.2 Hz, 1H), 3.65 (s, 3H), 3.38 (dq, J=7.1, 3.1 Hz, 1H), 3.21 (d, J=5.7 Hz, 2H), 2.90 (t, J=4.6 Hz, 1H), 2.77 (dd, J=5.0, 2.7 Hz, 1H), 1.41 (s, 9H).; $^{13}$C NMR (100 MHz, CDCl$_3$) δ 170.0, 155.5, 153.1, 131.8, 128.1, 124.0, 113.0, 112.96, 112.2, 109.9, 102.3, 80.1, 70.0, 69.9, 54.4, 52.4, 50.6, 44.9, 28.5, 28.3. HRMS (TOF MS ES+) m/z calcd for C$_{20}$H$_{27}$N$_2$O$_6$ [M+H]$^+$ 391.1869, found 391.1874.

Methyl 3-(5-allyloxy-1H-indol-3-yl)-2-tert-butoxycarbonylaminopropanoate (44)

To a stirred solution of 41 (200 mg, 0.60 mmol) in dry DMF (6 mL) were added cesium carbonate (390 mg, 1.2 mmol) and allyl bromide (0.12 mL, 1.40 mmol). The reaction mixture was stirred at 60° C. for 12 h, cooled to rt and concentrated under reduced pressure. It was diluted with ethyl acetate and worked up in usual manner and subjected to column chromatography with silica gel using 30% ethyl acetate in hexane as eluent to afford 44 (182 mg, 82%) as a yellow semi solid. $^1$H NMR (400 MHz, CDCl$_3$) δ 8.11 (s, 1H), 7.22 (d, J=8.8 Hz, 1H), 7.03 (s, 1H), 6.96 (d, J=2.5 Hz, 1H), 6.88 (dd, J=8.8, 2.3 Hz, 1H), 6.11 (ddt, J=16.3, 10.6, 5.3 Hz, 1H), 5.45 (dd, J=17.3, 1.9 Hz, 1H), 5.36-5.23 (m, 1H), 5.10 (d, J=8.3 Hz, 1H), 4.64 (d, J=7.2 Hz, 1H), 4.58 (d, J=5.4 Hz, 2H), 3.68 (s, 3H), 3.23 (d, J=5.5 Hz, 2H), 1.42 (s, 9H).; $^{13}$C NMR (100 MHz, CDCl$_3$) δ 173.0, 155.5, 153.3, 134.1, 131.6, 128.2, 123.8, 117.6, 113.3, 112.1, 110.1, 102.3, 80.1, 70.0, 54.4, 52.5, 28.5, 28.3.; HRMS (TOF MS ES+) m/z calcd for C$_{20}$H$_{27}$N$_2$O$_5$ [M+H]$^+$ 375.1920, found 375.1916.

Analogue 60 (12 mg, 10%) was prepared as a yellow solid from MTMSA (2) (90 mg, 0.09 mmol) using PyBop (72 mg, 0.14 mmol), NH$_2$-Phe-Trp-OMe (100 mg, 0.27 mmol) and DMF (5 mL), following the general procedure D. Mp: 154° C.; $^1$H NMR (600 MHz, CD$_3$OD) δ 7.51 (d, J=7.8 Hz, 1H), 7.37-7.25 (m, 5H), 7.14-7.10 (m, 2H), 7.07-7.04 (m, 1H), 6.69 (t, J=7.8 Hz, 1H), 6.41 (s, 1H), 6.26 (s, 1H), 5.07-5.00 (m, 2H), 4.84-4.79 (m, 2H), 4.77-4.67 (m, 2H), 4.40 (brs, 1H), 4.08 (dd, J=8.7, 5.3 Hz, 1H), 3.99 (brs, 1H), 3.91-3.86 (m, 2H), 3.82-3.78 (m, 2H), 3.76-3.70 (m, 4H), 3.69 (s, 3H), 3.67-3.59 (m, 3H), 3.55-3.51 (m, 1H), 3.45-3.40 (m, 2H), 3.38 (s, 3H), 3.29-3.21 (m, 6H), 3.17-3.10 (m, 3H), 3.03-2.97 (m, 3H), 2.65-2.60 (m, 1H), 2.47-2.45 (m, 1H), 2.39-2.34 (m, 2H), 2.28-2.10 (5H), 2.02-1.80 (m, 6H), 1.66-1.62 (m, 4H), 1.44 (d, J=6.1 Hz, 3H), 1.40 (d, J=5.6 Hz, 3H), 1.37 (d, J=6.1 Hz, 3H), 1.33 (d, J=7.3 Hz, 3H), 1.30 (d, J=6.2 Hz, 3H), 1.28 (s, 3H).; $^{13}$C NMR (100 MHz, CD$_3$OD) δ 204.3, 174.3, 173.7, 173.5, 169.6, 164.7, 160.3, 156.7, 139.4, 139.0, 138.1, 137.9, 136.3, 135.5, 130.6, 130.5, 130.2, 129.7, 128.9, 128.7, 128.6, 127.8, 124.8, 124.5, 122.6, 122.5, 119.9, 119.9, 119.2, 119.1, 118.3, 112.4, 112.4, 111.8, 110.4, 109.0, 108.6, 102.0, 100.1, 99.9, 98.9, 98.1, 80.9, 80.8, 78.1, 77.9, 77.4, 76.6, 76.4, 73.7, 73.4, 72.1, 72.0, 71.9, 71.8, 70.5, 60.4, 55.5, 55.0, 54.9, 52.9, 49.9, 47.9, 45.2, 44.8, 40.8, 38.6, 38.2, 33.2, 28.6, 28.5, 27.3, 18.8, 18.8, 18.2, 17.1. HRMS (TOF MS ES−) m/z calcd for C$_{70}$H$_{90}$N$_3$O$_{25}$ [M−H]$^-$ 1372.5863, found 1372.5890.

Analogue 61 (17 mg, 14%) was prepared as a yellow solid from MTMSA (2) (90 mg, 0.09 mmol) using PyBop (72 mg, 0.14 mmol), NH$_2$-Trp-Trp-OMe (110 mg, 0.27 mmol) and DMF (5 mL), following the general procedure D. Mp: 165° C.; $^1$H NMR (600 MHz, CD$_3$OD) δ 7.72 (d, J=7.9 Hz, 1H), 7.50 (d, J=7.8 Hz, 1H), 7.46 (d, J=8.2 Hz, 1H), 7.28 (d, J=8.1 Hz, 1H), 7.23 (d, J=7.1 Hz, 2H), 7.09 (d, J=8.9 Hz, 3H), 7.01 (t, J=7.7 Hz, 1H), 6.55 (s, 1H), 5.91 (s, 1H). 5.29 (brs, 1H), 5.06 (brs, 1H), 5.01-5.00 (m, 2H), 4.83 (t, J=6.6 Hz, 1H), 4.79 (d, J=9.8 Hz, 1H), 4.71-4.62 (m, 1H), 4.41 (d, J=11.1 Hz, 1H), 4.00 (s, 1H), 3.90-3.80 (m, 2H), 3.76-3.69 (m, 2H), 3.68 (s, 3H), 3.63-3.57 (m, 2H). 3.42-3.35 (m, 4H), 3.29-3.26 (m, 3H), 3.19-3.14 (m, 2H), 3.07 (t, J=8.7 Hz, 1H), 3.02-2.93 (m, 2H), 2.57-2.47 (m, 1H), 2.34-2.13 (m, 5H), 1.97-1.93 (m, 2H), 1.90-1.85 (m, 1H), 1.80 (q, J=11.3 Hz, 1H), 1.72 (d, J=15.1 Hz, 1H), 1.64-1.53 (m, 3H), 1.46 (d, J=6.1 Hz, 3H), 1.37-1.27 (m, 15H).; $^{13}$C NMR (100 MHz, CD$_3$OD) δ 204.0, 174.2, 173.9, 173.7, 160.2, 139.6, 138.2, 137.9, 136.4, 128.9, 128.8, 125.0, 124.8, 122.7, 122.5, 120.1, 119.9, 119.8, 119.2, 112.6, 112.4, 111.5, 111.1, 110.4, 109.1, 101.8, 100.0, 100.0, 99.0, 97.9, 80.9, 78.2, 77.9, 77.6, 77.4, 76.6, 76.3, 73.7, 73.3, 72.1, 72.0, 71.9, 71.8, 70.4, 64.4, 60.4, 54.9, 54.5, 52.9, 49.9, 47.4, 47.4, 45.3, 40.7, 38.2, 38.1, 33.2, 28.5, 27.4, 27.3, 27.3, 18.8, 18.7, 18.2, 18.2, 17.1. HRMS (TOF MS ES−) m/z calcd for C$_{72}$H$_{91}$N$_4$O$_{25}$ [M−H]$^-$ 1411.5972, found 1411.5985.

Isolation of MTMSA (2) from S. argillaceus M7W1[9]

S. argillaceus M7W1 colonies were selected by multiple spore to spore passages over RSA agar plates supplied with 50 µg/ml apramycin. The visually darkest colony was cultured for 48 h (30° C., 220 rpm) in TSB media supplemented with 50 µg/ml apramycin and subsequently used to inoculate a modified RSA media (100 g/L sucrose, 5 g/L glucose, 5 g/L soybean powder, 1 g/L yeast extract, 15 g/L MOPS, 5 g/L glycerol, 5 g/L MgCl$_2$.6H$_2$O, 1 g/L CaCO$_3$, pH 7.5) for 8 days (30° C., 240 rpm). The culture broth was centrifuged (3500 rpm, 30 min), the supernatant liquid was adjusted to pH 5.5 and extracted with n-BuOH (2×equal volume). The butanol fraction was concentrated under reduced pressure and purified with silica gel chromatography (gradient: Chloroform:Methanol:Acetic acid=15:1:0.1 to 10:1:0.1) to obtain 90% pure MTMSA (2), which was further purified by HPLC[15] to obtain pure MTMSA (2, yellow solid, 20 mg/L).

Cell Culture Media and Materials

RPMI-1640 (Sigma, St. Louis, Mo.), DMEM (Sigma, St. Louis, Mo.), and F12K (Sigma, St. Louis, Mo.) media were prepared with 10% v/v heat-inactivated fetal bovine serum (FBS) (Atlanta Biologicals, Flowery Branch, Ga.) and 1% v/v 10,000 units/mL penicillin and 10,000 µg/mL streptomycin (PS) (Life Technologies, Carlsbad, Calif.). McCoy's 5A (Sigma, St. Louis, Mo.) medium was prepared with 15% v/v FBS and 1% v/v PS. All media were prepared with 1.5-2 g/L sodium bicarbonate (Sigma, St. Louis, Mo.), pH was adjusted to 7.2 and filtered with 0.2 µm filters (Corning, Corning, N.Y.) prior to use. TC-32 (RPMI-1640), RD-ES (RPMI-1640), TC-71 (RPMI-1640), A-673 (DMEM), and 5838 (McCoy's 5A) cell lines (culture medium) were gifts from Dr. Timothy Cripe (Hospital Research Foundation, Columbus, Ohio). ES-8 (RPMI-1640), ES-2 (RPMI-1640), and ES-7 (RPMI-1640) were gifts from Dr. Peter Houghton (Greehey Children's Cancer Research Institute, San Antonio, Tex.). VCaP (DMEM), PC-3 (RPMI-1640), DU 145 (RPMI-1640), PANC-1 (DMEM), U-118 MG (DMEM), HeLa (DMEM), A549 (F12K), and DMS 114 (RPMI-1640) cell lines were from ATCC (Manassas, Va.). LNCaP (RPMI-1640) cell line was a gift from Dr. Vivek Rangnekar (University of Kentucky College of Medicine, Lexington, Ky.). HCT 116 (McCoy's 5A) cell line was a gift from the Genetic Resource Core Facility (Dr. Bert Vogelstein, John Hopkins School of Medicine, Baltimore, Md.). All cell lines were grown at 37° C. under 5% CO$_2$ in a humid incubator and were tested regularly for mycoplasma using the MycoAlert mycoplasma detection kit (Lonza, Basel, Switzerland).

72 h Growth Inhibition ($GI_{50}$) Assay

Cells were seeded in clear 96-well plates (VWR, Radnor, Pa.) at a cell density appropriate for exponential growth over 5 days. Following a 24 h attachment period, cells in duplicate wells were treated with half-log increments of respective compounds (0 nM and 0.3 nM-10 µM). Working stocks were prepared from an initial 10 mM drug stock diluted in either 100% EtOH or DMSO. All wells contained a final concentration of 0.1% v/v respective organic solvent. Immediately following treatment, cell viability was measured for (Day 0) no-treatment control wells. Cell viability was measured in the remaining wells after 72 h of incubation with compound or vehicle control. For viability measurements, 0.1 mM resazurin (Sigma, St. Louis, Mo.) was added to wells and following 3 h of incubation at 37° C., fluorescence readings (EM 560 nm, EX 590 nm) were recorded using a SpectraMax M5 plate reader (Molecular Devices, Sunnyvale, Calif.). Percent cell viability, relative to the initial seeding concentration, was calculated using the following formula:

$$\text{Percent Viability (\%)} = \frac{(Treatment_{Day\ 3} - Vehicle\ Control_{Day\ 0})}{(Vehicle\ Control_{Day\ 3} - Vehicle\ Control_{Day\ 0})} \times 100$$

Percent cell viability was plotted against concentration (Log [M]) and regression software GraphPad Prism 7.0 (GraphPad Software, La Jolla, Calif.) was used to curve fit data and calculate a respective 72 h growth inhibition ($GI_{50}$).

In Vitro Selectivity Screen Using Ewing Sarcoma $GI_{50}$ Model

The $GI_{50}$ of MTMSA (2) analogues was estimated first in TC-32 cells. Analogues with $GI_{50}$ values less than 250 nM in TC-32 cells were further tested in PC-3 cells. The ratio of $GI_{50}$ values (PC-3: TC-32) was then estimated and MTMSA (2) analogues with a ratio greater than 3 were selected for additional testing. A selectivity index for the compounds was then determined by taking the ratio of the median $GI_{50}$ found in the non-Ewing sarcoma cell lines compared to the median $GI_{50}$ found in ETS dependent cell lines.

Statistical Analysis of $GI_{50}$ Results

The $GI_{50}$ value was determined by pooling all available experiments and reported with 95% confidence interval. All compounds were tested at least once in multiwall replicates and each experiment included one or two control compounds (i.e., MTM (1) or MTMSA-Trp (3)) to ensure the stable response of the cell lines. The selectivity index was estimated by measuring the ratio of $GI_{50}$ estimates in non-Ewing sarcoma/ETS dependent cell lines. Median values are reported since the $GI_{50}$ was not estimable in, some cases.

Cloning of NR0B1 and CMV Promoter-Driven Luciferase Reporter Vectors

Full-length NR0B1 promoter sequence was PCR amplified using Q5 high-fidelity DNA polymerase (New England Biolabs, Ipswich, Mass.) from genomic DNA of TC-32 cells and cloned into the pGLUC-Basic 2 vector (New England Biolabs, Ipswich, Mass.). XhoI and KpnI restriction sites were incorporated into the primers. After restriction enzyme (New England Biolabs, Ipswich, Mass.) digest and purification by gel electrophoresis, the target amplicon was ligated into the pGLUC-Basic 2 vector using T4 DNA ligase (Thermo Fisher Scientific, Waltham, Mass.). Chemically competent TOP10 *E. coli* cells were used to propagate vectors under ampicillin selection (100 µg/mL) (Thermo Fisher Scientific, Waltham, Mass.). The resulting vectors were extracted and purified using GeneJET plasmid prep kit (Thermo Fisher Scientific, Waltham, Mass.). The purified vector was transfected into TC-32 cells using lipofectamine 3000 (Thermo Fisher Scientific, Waltham, Mass.) with subsequent G418 selection (1 mg/mL) (VWR, Radnor, Pa.). Separately, TC-32 cells were transfected with pCMV-Red Firefly Vector (Thermo Fisher Scientific, Waltham, Mass.) with subsequent puromycin selection (0.1 mg/mL) (Sigma, St. Louis, Mo.) as a control.

Luciferase Reporter Assay in Stably Transfected TC-32 Cells

Selected TC-32 cells, expressing either NR0B1 or CMV luciferase reporter vectors, were seeded in clear 96-well plates at a density of 10,000 cells/well. Following a 24 h attachment period, cells were treated in duplicate with half-log increments of respective compounds (0 nM and 0.3 nM-10 µM). After a 12 h treatment, media was removed and cells were washed 3 times with DPBS (Thermo Fisher Scientific, Waltham, Mass.). Cells were directly lysed on a plate shaker for 30 min at room temperature using 100 µL of passive membrane lysis solution. Lysates (80 µL) were transferred to a white luminescence plate. Luciferase substrate, either coelenterazine or D-luciferin (50 µL of 1× solution), for NR0B1 or CMV vectors, respectively, was added in a Glomax 96 microplate luminometer (Promega, Madison, Wis.) and luminescence was immediately measured. Delay before and after injections were set to the default of 0.4 s and a 10 s integration time was used. All reagents used in this assay were from the dual luciferase reporter assay system (Promega, Madison, Wis.). Concurrently, an additional 96 well plate was seeded and treated under the exact same conditions to determine cell viability using resazurin assay. Luminescence results were normalized to cell viability.

Relative mRNA Expression (qRT-PCR)

TC-32 cells were seeded in 6-well plates at a density of 300,000 cells/well. When 80% confluent, ~72 h later, cells were washed with DPBS and treated with respective compounds (0 nM and $GI_{50}$ nM). After 6 and 12 h treatments media was removed. Cells were washed with DPBS and 500 µL of 0.05% Trypsin with 0.53 mM EDTA (Corning, Corning, N.Y.) was added. After a 2-3 min incubation, cells detached from the plate and 1 mL of fresh RPMI media was immediately added. Cells were collected in 1.5 mL tubes on ice and centrifuged to a pellet at 1200× g for 5 min. Supernatant was removed and cell pellets were lysed with 600 µL of RLT lysis buffer (Qiagen, Hilden, Germany). Lysates were centrifuged through QIAshredder inserts for complete cell disruption (Qiagen, Hilden, Germany). RNeasy mini spin columns were used to isolate pure RNA (Qiagen, Hilden, Germany). RNA concentrations were measured using NanoDrop 2000 Spectrometer (Thermo Fisher Scientific, Waltham, Mass.) and a 100 ng/µL stock solution was prepared. RNA (1 μg) was used to prepare cDNA with a MultiScribe reverse transcriptase (Thermo Fisher Scientific, Waltham, Mass.). qRT-PCR reactions were conducted using Maxima SYBR green Taq DNA Polymerase (Thermo Fisher Scientific, Waltham, Mass.). EpMotion5070 (Eppendorf, Hamburg, Germany) robot was used to mix reactions in 384 well plates and thermocycling was completed on a QuantStudio 7 Flex (Thermo Fisher Scientific, Waltham, Mass.). GAPDH served as the housekeeping gene for comparing relative expression of target genes. All primers (IDT, Coralville, Iowa) were verified to amplify a single amplicon of appropriate size by gel electrophoresis and melting curve analysis.

| | LCMS data of free amines | | |
|---|---|---|---|
| Entry | Amine | LCMS (ES+) m/z calcd for | LCMS Found |
| 1 | 11 | $C_{13}H_{17}N_2O_2$ [M + H]$^+$ 233.1 | 233.1 |
| 2 | 12 | $C_{19}H_{21}N_2O_2$ [M + H]$^+$ 309.1 | 309.1 |
| 3 | 13 | $C_{15}H_{19}N_2O_2$ [M + H]$^+$ 259.1 | 259.1 |
| 4 | 14 | $C_{17}H_{23}N_2O_2$ [M + H]$^+$ 287.2 | 287.1 |

LCMS data of free amines

| Entry | Amine | LCMS (ES+) m/z calcd for | LCMS Found |
|---|---|---|---|
| 5 | 7-allyl tryptophan methyl ester | $C_{15}H_{19}N_2O_2$ $[M + H]^+$ 259.1 | 259.1 |
| 6 | 7-phenyl tryptophan methyl ester | $C_{18}H_{19}N_2O_2$ $[M + H]^+$ 295.1 | 295.1 |
| 7 | 6-(4-phenyl-1H-1,2,3-triazol-1-yl) tryptophan methyl ester (23) | $C_{20}H_{20}N_5O_2$ $[M]^+$ 362.1 | 362.1 |
| 8 | 6-trifluoromethyl tryptophan methyl ester (27) | $C_{13}H_{14}F_3N_2O_2$ $[M + H]^+$ 287.1 | 287.0 |
| 9 | 5-nitro tryptophan methyl ester | $C_{12}H_{14}N_3O_4$ $[M + H]^+$ 264.1 | 264.0 |

LCMS data of free amines

| Entry | Amine | LCMS (ES+) m/z calcd for | LCMS Found |
|---|---|---|---|
| 10 | 5-methoxy tryptophan methyl ester | $C_{13}H_{17}N_2O_3$ [M + H]$^+$ 249.1 | 249.1 |
| 11 | benzo-fused tryptophan methyl ester | $C_{16}H_{17}N_2O_2$ [M + H]$^+$ 269.1 | 269.0 |
| 12 | H-Phe-Trp-OMe | $C_{21}H_{24}N_3O_3$ [M + H]$^+$ 366.1 | 366.1 |
| 13 | H-Trp-Phe-OMe | $C_{21}H_{24}N_3O_3$ [M + H]$^+$ 366.1 | 366.1 |
| 14 | H-Trp-Trp-OMe | $C_{23}H_{25}N_4O_3$ [M + H]$^+$ 405.2 | 405.1 |
| 15 | H-(N-Me-Trp)-(N-Me-Trp)-OMe | $C_{25}H_{29}N_4O_3$ [M + H]$^+$ 433.2 | 433.1 |
| 16 | H-Phe-Phe-OMe | $C_{19}H_{23}N_2O_3$ [M + H]$^+$ 327.2 | 327.1 |

-continued

| | LCMS data of free amines | | |
|---|---|---|---|
| Entry | Amine | LCMS (ES+) m/z calcd for | LCMS Found |
| 17 | 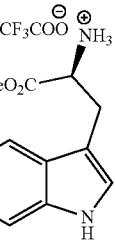 43 | $C_{17}H_{20}F_3N_2O_6$ [M + H]$^+$ 405.1 | 405.0 |
| 18 | 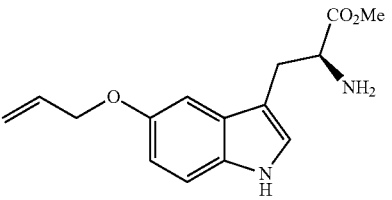 [SMILES: C=CCOc1ccc2[nH]cc(C[C@H](N)C(=O)OC)c2c1] | $C_{15}H_{19}N_2O_3$ [M + H]$^+$ 275.1 | 275.1 |
| 19 | 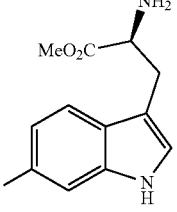 | $C_{12}H_{13}FN_2O_2$ [M]$^+$ 236.1 | 236.1 |
| 20 | 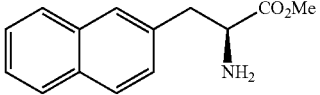 [SMILES: COC(=O)[C@@H](N)Cc1ccc2ccccc2c1] | $C_{14}H_{16}NO_2$ [M]$^+$ 230.1 | 230.1 |

| | HRMS data of analogues | | |
|---|---|---|---|
| Entry | MTMSA Analogues | HRMS-TOF MS | Yield |
| 1 | 50 | [M − H] calcd for $C_{61}H_{80}N_3O_{26}$ 1270.5030; Found 1270.5024 | 0.9 mg, 14% |
| 2 | 60 | [M − H] calcd for $C_{70}H_{90}N_3O_{25}$ 1372.5863; Found 1372.5890 | 12 mg, 10% |
| 3 | 59 | [M − H] calcd for $C_{70}H_{90}N_3O_{25}$ 1372.5863; Found 1372.5905 | 0.6 mg, 12% |
| 4 | 52 | [M − H] calcd for $C_{67}H_{85}N_2O_{24}$ 1301.5492; Found 1301.5460 | 3.4 mg, 26% |
| 5 | 53 | [M − H] calcd for $C_{64}H_{85}N_2O_{24}$ 1265.5492; Found 1265.5509 | 0.5 mg, 11% |
| 6 | 58 | [M − H] calcd for $C_{63}H_{82}NO_{24}$ 1236.5227; Found 1236.5288 | 1.6 mg, 16% |
| 7 | 46 | [M − H] calcd for $C_{68}H_{87}N_2O_{24}$ 1315.5649; Found 1315.5654 | 0.6 mg, 13% |

-continued

| | HRMS data of analogues | | |
|---|---|---|---|
| Entry | MTMSA Analogues | HRMS-TOF MS | Yield |
| 8 | 45 | [M − H] calcd for $C_{62}H_{83}N_2O_{24}$ Exact Mass: 1239.5336; Found 1239.5309 | 0.4 mg, 10% |
| 9 | 54 | [M − H] calcd for $C_{69}H_{86}N_5O_{24}$ 1368.5663; Found 1368.5635 | 0.9 mg, 18% |
| 10 | 61 | [M − H] calcd for $C_{72}H_{91}N_4O_{25}$ 1411.5972; Found 1411.5985 | 17 mg, 14% |
| 11 | 48a | [M − H] calcd for $C_{66}H_{89}N_2O_{24}$ 1293.5805; 1293.5876 | 0.6 mg, 12% |
| 12 | 48b | [M − H] calcd for $C_{66}H_{89}N_2O_{24}$ 1293.5805; 1293.5824 | 2.2 mg, 22% |
| 13 | 47 | [M − H] calcd for $C_{64}H_{85}N_2O_{24}$ 1265.5492; Found 1266.5557 | 0.4 mg, 10% |
| 14 | 57 | [M − H] calcd for $C_{65}H_{83}N_2O_{24}$ 1275.5336; Found 1275.5374 | 1.8 mg, 20% |
| 15 | 51 | [M − H] calcd for $C_{64}H_{85}N_2O_{25}$ 1281.5441 Found 1281.5485 | 2.2 mg, 22% |

HRMS data of analogues

| Entry | MTMSA Analogues | HRMS-TOF MS | Yield |
|---|---|---|---|
| 16 | 55 | [M − H] calcd for $C_{62}H_{80}F_3N_2O_{24}$ 1293.5053; Found 1293.5065 | 0.6 mg, 10% |
| 17 | 56 | [M − H] calcd for $C_{61}H_{80}FN_2O_{24}$ 1243.5085; Found 1243.5108 | 1.1 mg, 17% |
| 18 | 49 | [M − H] calcd for $C_{62}H_{83}N_2O_{25}$ 1255.5285; Found 1255.5267 | 1.5 mg, 14% |
| 19 | 62 | [M − H] calcd for $C_{74}H_{95}N_4O_{25}$ 1439.6285; Found 1439.6305 | 1.4 mg, 17% |
| 20 | 63 | [M − H] calcd for $C_{68}H_{89}N_2O_{25}$ 1333.5754; Found 1333.5756 | 0.4 mg, 10% |

TABLE 5

Cytotoxicity ($GI_{50}$) screen in Ewing sarcoma cell lines of select MTMSA analogues

| | RD-ES EWS-FLI1 Type 2 | | TC-71 EWS-FLI1 Type 1 | | A-673 EWS-FLI1 Type 1 | | 5838 EWS-ERG | | ES-8 EWS-FLI1 Type 2 | | ES-2 EWS-FLI1 Type 3 | | ES-7 EWS-FLI1 Type 4 | |
|---|---|---|---|---|---|---|---|---|---|---|---|---|---|---|
| MTMSA Analogues | $GI_{50}$ (nM) | CI (95%) | $GI_{50}$ (nM) | CI (95%) | $GI_{50}$ (nM) | CI (95%) | $GI_{50}$ (nM) | CI (95%) | $GI_{50}$ (nM) | CI (95%) | $GI_{50}$ (nM) | CI (95%) | $GI_{50}$ (nM) | CI (95%) |
| MTM (1) | 40 | 30-53 | 55 | 44-68 | 41 | 30-56 | 43 | 30-61 | 54 | 43-68 | 63 | 45-89 | 46 | 28-76 |
| MTMSAPhe (4) | 91 | 68-126 | 143 | 95-216 | 146 | 92-230 | 38 | 30-49 | 72 | 46-115 | 261 | 117-615 | 156 | 110-222 |
| MTMSATrp (3) | 47 | 26-85 | 57 | 40-82 | 81 | 35-186 | 6 | 4-10 | 99 | 60-162 | 133 | 77-231 | 32 | 12-92 |
| 60 | 50 | 32-76 | 44 | 25-82 | 168 | 124-230 | 149 | 121-186 | 53 | 46-61 | 78 | 66-91 | 46 | 22-104 |
| 61 | 57 | 44-75 | 35 | 18-68 | 364 | 186-714 | 53 | 40-70 | 114 | 89-147 | 123 | 74-204 | 48 | 29-83 |
| 59 | 54 | 31-95 | 19 | 7-71 | 238 | 175-321 | 39 | 25-60 | 74 | 46-120 | 125 | 69-228 | Ne | Ne |
| 45 | 539 | 416-703 | 696 | 534-987 | 1009 | 603-1717 | 121 | 98-151 | 1331 | 857-2090 | 1501 | 1081-2376 | 672 | 508-855 |
| 51 | 843 | 567-1264 | 636 | 436-937 | 272 | 214-357 | 24 | 20-29 | 90 | 54-152 | 5374 | >1377 | 1664 | 1024-2757 |
| 56 | 1004 | 700-1455 | 640 | 429-962 | 262 | 222-299 | 466 | 229-929 | 401 | 250-652 | 3310 | >1231 | 1657 | 1093-2547 |
| 63 | 3052 | 1026-13442 | 211 | 175-254 | 491 | 179-1339 | 579 | 350-966 | 542 | 426-675 | Ne | Ne | 910 | 340-2519 |

TABLE 6

Cytotoxicity ($GI_{50}$) screen in non-Ewing sarcoma cell lines of select MTMSA analogues

| | DU 145 | | HCT 116 | | PANC-1 | | U-118 MG | |
|---|---|---|---|---|---|---|---|---|
| MTMSA Analogues | $GI_{50}$ (nM) | CI (95%) | $GI_{50}$ (nM) | CI (95%) | $GI_{50}$ (nM) | CI (95%) | $GI_{50}$ (nM) | CI (95%) |
| MTM (1) | 26 | 20-35 | 32 | 26-38 | 100 | 89-113 | 80 | 52-114 |
| MTMSA Phe (4) | 315 | 222-482 | 256 | 189-311 | 261 | 213-317 | 1819 | 372-12206 |
| MTMSA Trp (3) | 46 | 39-56 | 30 | 24-36 | 161 | 102-254 | 167 | 87-325 |
| 60 | 400 | 199-816 | 449 | 289-699 | 574 | 453-742 | Ne | >422 |
| 61 | 246 | 139-439 | 198 | 125-314 | 640 | 519-786 | Ne | Ne |
| 59 | 67 | 39-115 | 82 | 73-84 | 152 | 74-311 | 830 | 569-987 |
| 45 | 761 | 629-894 | 826 | >620 | 1731 | >988 | Ne | Ne |
| 51 | 298 | 237-389 | 380 | 254-596 | 532 | 330-873 | 291 | 191-449 |
| 56 | 157 | 108-203 | 419 | 225-770 | 386 | 255-643 | 303 | 191-484 |
| 63 | 159 | 130-195 | 437 | 176-1052 | 1956 | 1793-2126 | 2204 | 1302-3846 |

| | HeLa | | A549 | | DMS 114 | | LNCaP | |
|---|---|---|---|---|---|---|---|---|
| MTMSA Analogues | $GI_{50}$ (nM) | CI (95%) | $GI_{50}$ (nM) | CI (95%) | $GI_{50}$ (nM) | CI (95%) | $GI_{50}$ (nM) | CI (95%) |
| MTM (1) | 77 | 66-89 | 71 | 59-85 | 65 | 42-101 | 48 | 31-75 |
| MTMSA Phe (4) | 545 | 307-982 | 1237 | 987-1952 | 483 | 254-935 | 732 | 382-1428 |
| MTMSA Trp (3) | 323 | 233-448 | 89 | 62-130 | 151 | 56-425 | 109 | 73-164 |
| 60 | 557 | 200-1616 | 2849 | 1905-41225 | 1135 | >366 | 1607 | 1054-2454 |
| 61 | 951 | 498-1858 | 1399 | 758-2646 | 1115 | 543-2384 | 856 | 603-1218 |
| 59 | 397 | 282-625 | 1938 | 1668-2220 | 18 | 6-54 | 697 | 457-1064 |
| 45 | 1758 | 1463-2082 | 2372 | 1538-5217 | 1054 | 851-1404 | 1863 | 1263-2808 |
| 51 | 1709 | 1242-2490 | 1540 | 253-9711 | 2840 | 1316-6612 | 2228 | 1445-3526 |
| 56 | 1551 | 695-3647 | 941 | 363-2466 | 2468 | >649 | 1965 | 866-4942 |
| 63 | 1774 | 1195-2674 | Ne | Ne | 2310 | 1174-4815 | Ne | Ne |

TABLE 7

Primers used for qRT-PCR analysis

| Gene | Forward Primer | Reverse Primer |
|---|---|---|
| EWS-FLI1 | TCCTACAGCCAAGCTCCAAGTC | ACTCCCCGTTGGTCCCCTCC |
| NR0B1 | TGATGCTGGAAATGCTCTGT | TTACACTCTTTTGCCCACAGC |
| Sp1 | GGAGAGCAAAACCAGCAGAC | AAGGTGATTGTTTGGGCTTG |
| BCL-2 | GAGACAGCCAGGAGAAATCA | CCTGTGGATGACTGAGTACC |
| CCK | CTGCGTCCTAATCCAAAAGC | CATTCGTCCAGAAGGAGC |
| GAPDH | AAGGTGAAGGTCGGAGTCAA | GATCTCGCTCCTGGAAGATG |

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Wohlert, S.; Künzel, E.; Machinek, R.; Mendez, C.; Salas, J.; Rohr, J. The structure of mithramycin reinvestigated. *J. Nat. Prod.* 1999, 62, 119-121.
2. Rohr, J.; Méndez, C.; Salas, J. A. The biosynthesis of aureolic acid group antibiotics. *Bioorg. Chem.* 1999, 27, 41-54.
3. Kofman, S., Perlia, C. P, Economou, S. G. Mithramycin in the treatment of metastatic ewing's sarcoma. *Cancer* 1973, 31, 889-893.; b) Balamuth, N., Womer, R. B.: Ewing's sarcoma, *Lancet Oncol.* 2010, 11, 184-192.
4. (a) Kofman, S.; Eisenstein, R. Mithramycin in the treatment of disseminated cancer. *Cancer Chemother. Rep.* 1963, 32, 77-96.; (b) Kofman, S.; Medrek, T. J.; Alexander, R. W. Mithramycin in the treatment of embryonal cancer. *Cancer* 1964, 17, 938-948.
5. Delattre, O.; Zucman, J.; Plougastel, B.; Desmaze, C.; Melot, T.; Peter, M.; Kovar, H.; Joubert, I.; de Jong, P.; Rouleau, G. Gene fusion with an ETS DNA-binding domain caused by chromosome translocation in human tumours. *Nature* 1992, 359, 162.
6. May, W. A.; Arvand, A.; Thompson, A. D.; Braun, B. S.; Wright, M.; Denny, C. T. EWS/FLI1-induced manic fringe renders NIH 3T3 cells tumorigenic. *Nat. Genet.* 1997, 17, 495-497.
7. Tomlins, S. A., Rhodes, D. R., Perner, S., Dhanasekaran, S. M., Mehra, R., Sun, X. W., Varambally, S., Cao, X., Tchinda, J., Kuefer, R. and Lee, C. Recurrent fusion of TMPRSS2 and ETS transcription factor genes in prostate cancer. *Science*, 2005, 310, 644-648.
8. Sastry, M.; Patel, D. J. Solution structure of the mithramycin dimer-DNA complex. *Biochemistry* 1993, 32, 6588-6604.
9. Remsing, L. L.; González, A. M.; Nur-e-Alam, M.; Fernandez-Lozano, M. J.; Braña, A. F.; Rix, U.; Oliveira, M. A.; Méndez, C.; Salas, J. A.; Rohr, J. Mithramycin SK, a novel antitumor drug with improved therapeutic index, mithramycin SA, and demycarosyl-mithramycin SK: three new products generated in the mithramycin producer *Streptomyces argillaceus* through combinatorial biosynthesis. *J. Am. Chem. Soc.* 2003, 125, 5745-5753.
10. Scott, D.; Chen, J. M.; Bae, Y; Rohr, J. Semi-synthetic mithramycin SA derivatives with improved anti-cancer activity. *Chem. Biol. Drug. Des.* 2013, 81, 615-624.
11. Leggas, M.; Eckenrode, J.; Mitra, P.; Jha, J.; Salem, S.; Mandal, A.; Thorson, J.; Rohr, J. [abstract]. In: Proceedings of the AACR-NCI-EORTC international conference: molecular targets and cancer therapeutics; 2017 Oct. 26-30; philadelphia, Pa. philadelphia (Pa.): AACR; *Mol Cancer Ther.* 2018, 17 (1 Suppl):Abstract nr B043.
12. Hou, C.; Weidenbach, S.; Cano, K. E.; Wang, Z.; Mitra, P.; Ivanov, D. N.; Rohr, J.; Tsodikov, O. V. Structures of mithramycin analogues bound to DNA and implications for targeting transcription factor FLI1. *Nucleic Acids Res.* 2016, 44, 8990-9004.
13. Alqahtani, N.; Porwal, S. K.; James, E. D.; Bis, D. M.; Karty, J. A.; Lane, A. L.; Viswanathan, R. Synergism between genome sequencing, tandem mass spectrometry and bio-inspired synthesis reveals insights into nocardioazine B biogenesis. *Org. Biomol. Chem.* 2015, 13, 7177-7192.
14. Cardoso, A. S. P.; Marques, M. M. B.; Srinivasan, N.; Prabhakar, S.; Lobo, A. M.; Rzepa, H. S. Studies in sigmatropic rearrangements of N-prenylindole derivatives—a formal enantiomerically pure synthesis of tryprostatin B. *Org. Biomol. Chem.* 2006, 4, 3966-3972.
15. Loach, R. P.; Fenton, O. S.; Amaike, K.; Siegel, D. S.; Ozkal, E.; Movassaghi, M. Derivatization of C3-alkylindoles including tryptophans and tryptamines. *J. Org. Chem.* 2014, 79, 11254-11263.
16. Partridge, B. M.; Hartwig, J. F. Sterically controlled iodination of arenes via iridium-catalyzed C—H borylation. *Org. Lett.* 2012, 15, 140-143.
17. Feng, Y.; Holte, D.; Zoller, J.; Umemiya, S.; Simke, L. R.; Baran, P. S. Total synthesis of erruculogen and fumitremorgin a enabled by ligand-controlled CH borylation. *J. Am. Chem. Soc.* 2015, 137, 10160-10163.
18. Jia, Y.; Zhu, J. Palladium-catalyzed, modular synthesis of highly functionalized indoles and tryptophans by direct annulation of substituted o-haloanilines and aldehydes. *J. Org. Chem.* 2006, 71, 7826-7834.
19. Kokotos, G.; Padrón, J. M.; Martin, T.; Gibbons, W. A.; Martin, V. S. A general approach to the asymmetric synthesis of unsaturated lipidic α-amino acids. The first synthesis of α-aminoarachidonic acid. *J. Org. Chem.* 1998, 63, 3741-3744.
20. Bi, W.; Bi, Y.; Xue, P.; Zhang, Y.; Gao, X.; Wang, Z.; Li, M.; Baudy-Floc'h, M.; Ngerebara, N.; Li, X. Novel β-carboline-tripeptide conjugates attenuate mesenteric ischemia/reperfusion injury in the rat. *Eur. J. Med. Chem.* 2011, 46, 2441-2452.
21. Coste, A.; Toumi, M.; Wright, K.; Razafimahaléo, V.; Couty, F.; Marrot, J.; Evano, G. Copper-catalyzed cyclization of iodo-tryptophans: A straightforward synthesis of pyrroloindoles. *Org. Lett.* 2008, 10, 3841-3844.
22. Cozett, R. E.; Venter, G. A.; Gokada, M. R.; Hunter, R. Catalytic enantioselective acyl transfer: the case for 4-PPY with a C-3 carboxamide peptide auxiliary based on synthesis and modelling studies. *Org. Biomol. Chem.* 2016, 14, 10914-10925.
23. Choi, J. Y.; Calvet, C. M.; Gunatilleke, S. S.; Ruiz, C.; Cameron, M. D.; McKerrow, J. H.; Podust, L. M.; Roush, W. R. Rational development of 4-aminopyridyl-based inhibitors targeting *Trypanosoma cruzi* CYP51 as anti-chagas agents. *J. Med. Chem.* 2013, 56, 7651-7668.

24. Osgood, C. L.; Maloney, N.; Kidd, C. G.; Kitchen-Goosen, S.; Segars, L.; Gebregiorgis, M.; Woldemichael, G. M.; He, M.; Sankar, S.; Lessnick, S. L.; Kang, M.; Smith, M.; Turner, L.; Madaj, Z. B.; Winn, M. E.; Núñez, L. E.; González-Sabín, Z.; Helman, L. J.; Morís, F.; Grohar, P. J. Identification of mithramycin analogues with improved targeting of the EWS-FLI1 transcription factor. *Clin. Cancer Res.* 2016, 22, 4105-4118.

25. Garcia-Aragoncillo, E., J. Carrillo, E. Lalli, N. Agra, G. Gomez-Lopez, A. Pestana, and J. Alonso. "DAX1, a direct target of EWS/FLI1 oncoprotein, is a principal regulator of cell-cycle progression in ewing's tumor cells." *Oncogene* 2008, 27, 6034-6043.

26. Grohar, P. J.; Woldemichael, G. M.; Griffin, L. B.; Mendoza, A.; Chen, Q.-R.; Yeung, C.; Currier, D. G.; Davis, S.; Khanna, C.; Khan, J. Identification of an inhibitor of the EWS-FLI1 oncogenic transcription factor by high-throughput screening. *J. Natl. Cancer Inst.* 2011, 103, 962-978.

27. U.S. Pat. No. 9,447,135 to Rohr, J. T, et al., "Semi-Synthetic Mithramycin Derivatives with Anti-Cancer Activity."

It will be understood that various details of the presently disclosed subject matter can be changed without departing from the scope of the subject matter disclosed herein. Furthermore, the foregoing description is for the purpose of illustration only, and not for the purpose of limitation.

SEQUENCE LISTING

```
SEQ ID NO: 01:
  1   pgsgqiglwq fllellsdsa nascitwegt ngefkmtdpd evarrwgerk skpnmnydkl sralryyydk nimtkvhgkr yaykfdfhgi aqalqphp        98

SEQ ID NO: 02
  1   pgsgqiglwq fllellsdss nsscitwegt ngefkmtdpd evarrwgerk skpnmnydkl sralryyydk nimtkvhgkr yaykfdfhgi aqalqphp        98

SEQ ID NO: 03-amino acid sequence of FLI1 transcription factor,
with the DNA binding domain in that sequence highlighted.
  1   mdgtikeals vvsddqslfd saygaaahlp kadmtasgsp dygqphkinp lppqqewinq 61   pvrvnvkrey dhmngsresp vdcsvskcsk lvgggesnpm nynsymdekn gppppnmttn 121   errvivpadp tlwtqehvrg wlewaikeys lmeidtsffq nmdgkelckm nkedflratt 181   lyntevllsh lsylressll aynttshtdq ssrlsvkedp sydsvrrgaw gnnmnsglnk 241   spplggaqti sknteqrpqp dpyqilgpts srlanpgsgq iqlwqfllel lsdsanasci 301   twegtngefk mtdpdevarr wgerkskpnm nydklsralr yyydknimtk vhgkryaykf 361   dfhgiaqalg phptessmyk ypsdisymps yhahqqkvnf vpphpssmpv tsssffgaas 421   qywtsptggi ypnpnvprhp nthvpshlgs yy SEQ ID NO: 04-amino acid sequence of ERG transcription factor,
with the DNA binding domain in that sequence highlighted.
  1   miqtvpdpaa hikealsvvs edqslfecay gtphlaktem tassssdygq tskmsprvpg 61   qdwlsqppar vtikmecnps qvngsrnspd ecsvakggkm vgspdtvgmn ygsymeekhm 121   pppnmttner rvivpadptl wstdhvrqwl ewavkeyglp dvnillfgni dgkelckmtk 181   ddfgrltpsy nadillshlh ylretplphl tsddvdkalq nsprlmharn tdlpyepprr 241   sawtghghpt pqskaagpsp stvpktedqr pqldpyqilg ptssrlanpg sgglqlwqfl 301   lellsdssns scitwegtng efkmtdpdev arrwgerksk pnmnydklsr alryyydkni 361   mtkvhgkrya ykfdfhgiaq alqphppess lykypsdlpy mgsyhahpqk mnfvaphppa 421   lpvtsssffa apnpywnspt ggiypntrlp tshmpshlgt yy
```

What is claimed is:

1. A mithramycin side chain carboxylic acid (MTM SA) derivative having the following formula:

MTM-SA-R' or a pharmaceutically acceptable salt thereof, wherein R' is
  (a) a substituted tryptophan (Trp) or phenylalanine (Phe) derivative having a substitution on a phenyl or indole ring of the amino acid derivative, wherein the substitution is selected from the group consisting of lower alkyl, prenyl, aryl, alkylaryl, alkoxyl, nitro, halogen, and halocarbon;
  (b) a substituted Trp, Phe, Trp-Phe, or Phe-Trp dipeptide derivative having a substitution on a phenyl or indole ring of the amino acid dipeptide derivative, wherein the substitution is selected from the group consisting of lower alkyl, prenyl, aryl, alkylaryl, alkoxyl, nitro, halogen, and halocarbon; or
  (c) an unsubstituted Trp, Phe, Trp-Phe, or Phe-Trp dipeptide derivative.

2. The MTM-SA derivative of claim 1, wherein R' is a substituted tryptophan (Trp) derivative.

3. The MTM-SA derivative of claim 2, having the following formula:

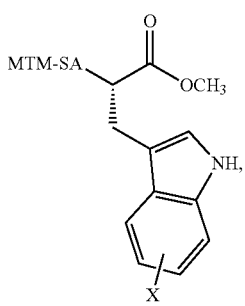

wherein X is selected from lower alkyl, prenyl, aryl, alkylaryl, alkoxyl, nitro, halogen, and halocarbon.

4. The MTM-SA derivative of claim 3, wherein X is selected from methyl, allyl, O-allyl, prenyl, 5,6-benzo, benzyl, phenyl, phenyl-triazole, F, and $CF_3$.

5. The MTM-SA derivative of claim 1, selected from the formulae consisting of:

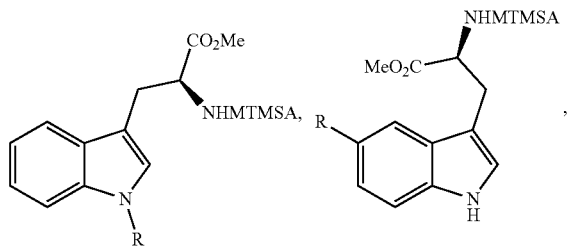

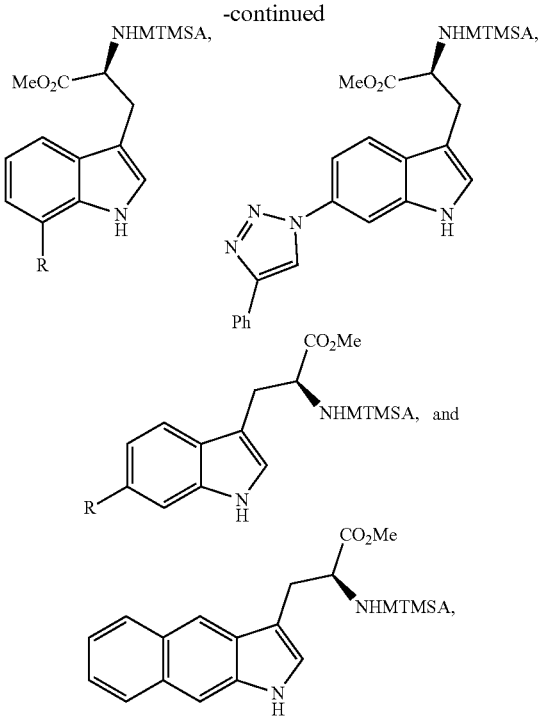

wherein R is selected from the group consisting of methyl, allyl, O-allyl, prenyl, benzyl, phenyl, phenyl-triazole, F, and $CF_3$.

6. The MTM-SA derivative of claim 1, having the following formula:

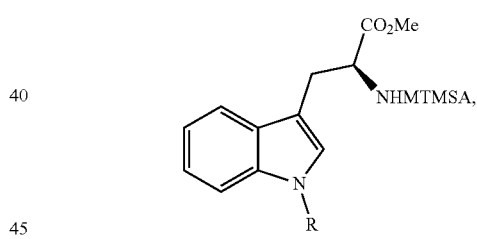

wherein R is selected from the group consisting of methyl, benzyl, allyl, and prenyl.

7. The MTM-SA derivative of claim 1, having the following formula:

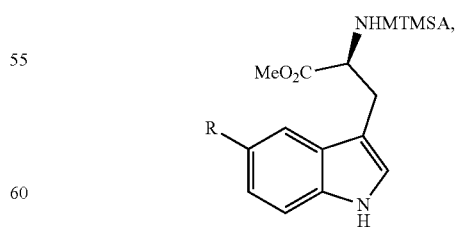

wherein R is selected from the group consisting of OMe, $NO_2$, and O-allyl.

8. The MTM-SA derivative of claim 1, having the following formula:

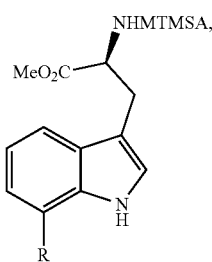

wherein R is selected from the group consisting of phenyl and allyl.

9. The MTM-SA derivative of claim 1, having the following formula:

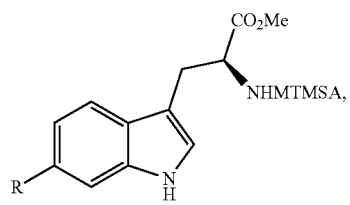

wherein R is selected from the group consisting of F and CF$_3$.

10. The MTM-SA derivative of claim 1, wherein R' is a substituted phenylalanine (Phe) derivative.

11. The MTM-SA derivative of claim 10, having the following formula:

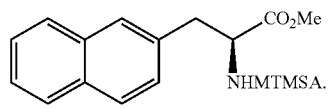

12. The MTM-SA derivative of claim 1, wherein R' is a substituted Trp, Phe, Trp-Phe, or Phe-Trp dipeptide derivative or an unsubstituted Trp, Phe, Trp-Phe, or Phe-Trp dipeptide derivative.

13. The MTM-SA derivative of claim 1, selected from the formulae consisting of:

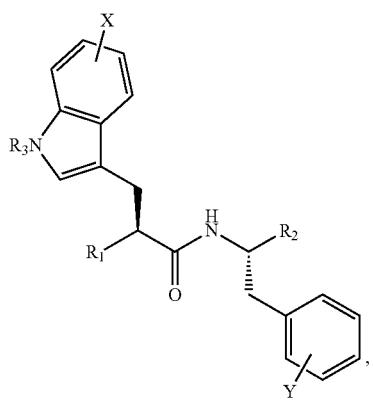

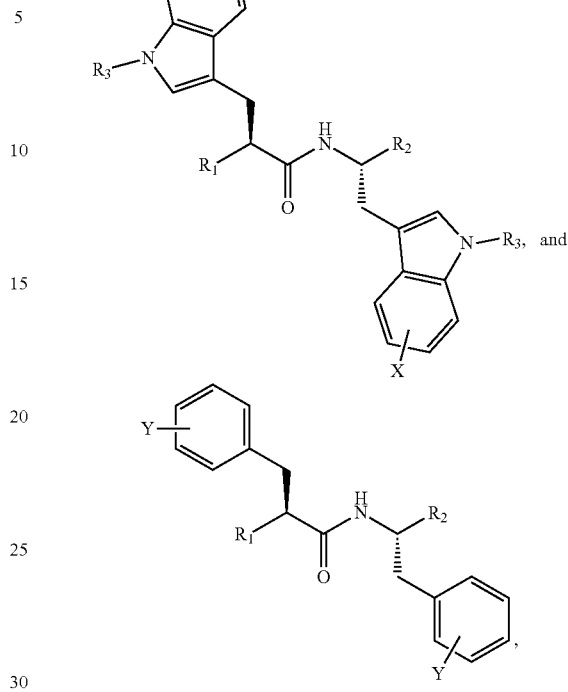

wherein one of R$_1$ and R$_2$ is MTM-SA, and the other of R$_1$ and R$_2$ is CO$_2$CH$_3$; R$_3$ is H or Me; X is selected from the group consisting of methyl, allyl, O-allyl, prenyl, 5,6-benzo, benzyl, phenyl, phenyl-triazole, F, and CF$_3$; and Y is selected from the group consisting of H and 3, 4-benzo.

14. The MTM-SA derivative of claim 1, wherein R' is a substituted Trp, Phe, Trp-Phe, or Phe-Trp dipeptide derivative having a substitution on a phenyl or indole ring of the Trp, Phe, Trp-Phe, or Phe-Trp dipeptide derivative, wherein the substitution is selected from the group consisting of lower alkyl, prenyl, aryl, alkylaryl, alkoxyl, nitro, halogen, and halocarbon; or an unsubstituted Trp, Phe, Trp-Phe, or Phe-Trp dipeptide derivative.

15. A method of treating cancer or neuro-disease in a patient in need thereof, the method comprising administering to the patient a therapeutically effective amount of the MTM-SA derivative or a pharmaceutically acceptable salt thereof of claim 1.

16. The method of claim 15, wherein the method comprises treating Ewing sarcoma.

17. The method of claim 15, wherein the method comprises treating lung cancer.

18. The method of claim 15, wherein the method comprises treating leukemia or lymphoma.

19. The method of claim 15, wherein the method comprises treating colon cancer.

20. A method for selectively modulating the activity of a target ETS transcription factor in a patient in need thereof, including administering to the patient a therapeutically effective amount of an MTM-SA derivative or a pharmaceutically acceptable salt thereof of claim 1.

* * * * *

UNITED STATES PATENT AND TRADEMARK OFFICE
CERTIFICATE OF CORRECTION

| | |
|---|---|
| PATENT NO. | : 11,224,609 B2 |
| APPLICATION NO. | : 16/122655 |
| DATED | : January 18, 2022 |
| INVENTOR(S) | : Rohr et al. |

It is certified that error appears in the above-identified patent and that said Letters Patent is hereby corrected as shown below:

In the Specification

Replace the second paragraph, which appears on Column 1, with the following:
Government Interest
This invention was made with government support under grant numbers CA 243529 awarded by the National Institutes of Health, and grant numbers W81XWH1610477, W81XWH1610478, W81XWH1610479 awarded by the Department of Defense, Department of Army. The government has certain rights in the invention.

Signed and Sealed this
Second Day of August, 2022

Katherine Kelly Vidal
*Director of the United States Patent and Trademark Office*

SEQUENCE LISTING

<160> NUMBER OF SEQ ID NOS: 4

<210> SEQ ID NO 1
<211> LENGTH: 98
<212> TYPE: PRT
<213> ORGANISM: Homo sapiens

<400> SEQUENCE: 1

Pro Gly Ser Gly Gln Ile Gln Leu Trp Gln Phe Leu Leu Glu Leu Leu

-continued

```
                 1               5                  10                  15
            Ser Asp Ser Ala Asn Ala Ser Cys Ile Thr Trp Glu Gly Thr Asn Gly
                         20                  25                  30

Glu Phe Lys Met Thr Asp Pro Asp Glu Val Ala Arg Arg Trp Gly Glu
                         35                  40                  45

Arg Lys Ser Lys Pro Asn Met Asn Tyr Asp Lys Leu Ser Arg Ala Leu
                         50                  55                  60

Arg Tyr Tyr Tyr Asp Lys Asn Ile Met Thr Lys Val His Gly Lys Arg
             65                  70                  75                  80

Tyr Ala Tyr Lys Phe Asp Phe His Gly Ile Ala Gln Ala Leu Gln Pro
                                 85                  90                  95

His Pro

<210> SEQ ID NO 2
<211> LENGTH: 98
<212> TYPE: PRT
<213> ORGANISM: Homo sapiens

<400> SEQUENCE: 2

Pro Gly Ser Gly Gln Ile Gln Leu Trp Gln Phe Leu Leu Glu Leu Leu
             1               5                  10                  15

Ser Asp Ser Ser Asn Ser Ser Cys Ile Thr Trp Glu Gly Thr Asn Gly
                         20                  25                  30

Glu Phe Lys Met Thr Asp Pro Asp Glu Val Ala Arg Arg Trp Gly Glu
                         35                  40                  45

Arg Lys Ser Lys Pro Asn Met Asn Tyr Asp Lys Leu Ser Arg Ala Leu
                         50                  55                  60

Arg Tyr Tyr Tyr Asp Lys Asn Ile Met Thr Lys Val His Gly Lys Arg
             65                  70                  75                  80

Tyr Ala Tyr Lys Phe Asp Phe His Gly Ile Ala Gln Ala Leu Gln Pro
                                 85                  90                  95

His Pro

<210> SEQ ID NO 3
<211> LENGTH: 452
<212> TYPE: PRT
<213> ORGANISM: Homo sapiens

<400> SEQUENCE: 3

Met Asp Gly Thr Ile Lys Glu Ala Leu Ser Val Val Ser Asp Asp Gln
             1               5                  10                  15

Ser Leu Phe Asp Ser Ala Tyr Gly Ala Ala His Leu Pro Lys Ala
                         20                  25                  30

Asp Met Thr Ala Ser Gly Ser Pro Asp Tyr Gly Gln Pro His Lys Ile
                         35                  40                  45

Asn Pro Leu Pro Pro Gln Gln Glu Trp Ile Asn Gln Pro Val Arg Val
                         50                  55                  60

Asn Val Lys Arg Glu Tyr Asp His Met Asn Gly Ser Arg Glu Ser Pro
             65                  70                  75                  80

Val Asp Cys Ser Val Ser Lys Cys Ser Lys Leu Val Gly Gly Gly Glu
                                 85                  90                  95

Ser Asn Pro Met Asn Tyr Asn Ser Tyr Met Asp Glu Lys Asn Gly Pro
                             100                 105                 110

Pro Pro Pro Asn Met Thr Thr Asn Glu Arg Arg Val Ile Val Pro Ala
                         115                 120                 125
```

```
Asp Pro Thr Leu Trp Thr Gln Glu His Val Arg Gln Trp Leu Glu Trp
    130                 135                 140

Ala Ile Lys Glu Tyr Ser Leu Met Glu Ile Asp Thr Ser Phe Phe Gln
145                 150                 155                 160

Asn Met Asp Gly Lys Glu Leu Cys Lys Met Asn Lys Glu Asp Phe Leu
                165                 170                 175

Arg Ala Thr Thr Leu Tyr Asn Thr Glu Val Leu Leu Ser His Leu Ser
            180                 185                 190

Tyr Leu Arg Glu Ser Ser Leu Leu Ala Tyr Asn Thr Thr Ser His Thr
        195                 200                 205

Asp Gln Ser Ser Arg Leu Ser Val Lys Glu Asp Pro Ser Tyr Asp Ser
    210                 215                 220

Val Arg Arg Gly Ala Trp Gly Asn Asn Met Asn Ser Gly Leu Asn Lys
225                 230                 235                 240

Ser Pro Pro Leu Gly Gly Ala Gln Thr Ile Ser Lys Asn Thr Glu Gln
                245                 250                 255

Arg Pro Gln Pro Asp Pro Tyr Gln Ile Leu Gly Pro Thr Ser Ser Arg
            260                 265                 270

Leu Ala Asn Pro Gly Ser Gly Gln Ile Gln Leu Trp Gln Phe Leu Leu
        275                 280                 285

Glu Leu Leu Ser Asp Ser Ala Asn Ala Ser Cys Ile Thr Trp Glu Gly
    290                 295                 300

Thr Asn Gly Glu Phe Lys Met Thr Asp Pro Asp Glu Val Ala Arg Arg
305                 310                 315                 320

Trp Gly Glu Arg Lys Ser Lys Pro Asn Met Asn Tyr Asp Lys Leu Ser
                325                 330                 335

Arg Ala Leu Arg Tyr Tyr Tyr Asp Lys Asn Ile Met Thr Lys Val His
            340                 345                 350

Gly Lys Arg Tyr Ala Tyr Lys Phe Asp Phe His Gly Ile Ala Gln Ala
        355                 360                 365

Leu Gln Pro His Pro Thr Glu Ser Ser Met Tyr Lys Tyr Pro Ser Asp
    370                 375                 380

Ile Ser Tyr Met Pro Ser Tyr His Ala His Gln Gln Lys Val Asn Phe
385                 390                 395                 400

Val Pro Pro His Pro Ser Ser Met Pro Val Thr Ser Ser Ser Phe Phe
                405                 410                 415

Gly Ala Ala Ser Gln Tyr Trp Thr Ser Pro Thr Gly Gly Ile Tyr Pro
            420                 425                 430

Asn Pro Asn Val Pro Arg His Pro Asn Thr His Val Pro Ser His Leu
        435                 440                 445

Gly Ser Tyr Tyr
    450

<210> SEQ ID NO 4
<211> LENGTH: 462
<212> TYPE: PRT
<213> ORGANISM: Homo sapiens

<400> SEQUENCE: 4

Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
            20                  25                  30

Pro His Leu Ala Lys Thr Glu Met Thr Ala Ser Ser Ser Ser Asp Tyr
        35                  40                  45
```

-continued

```
Gly Gln Thr Ser Lys Met Ser Pro Arg Val Pro Gln Gln Asp Trp Leu
        50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                        85                  90                  95

Gly Gly Lys Met Val Gly Ser Pro Asp Thr Val Gly Met Asn Tyr Gly
                100                 105                 110

Ser Tyr Met Glu Glu Lys His Met Pro Pro Asn Met Thr Thr Asn
                115                 120                 125

Glu Arg Arg Val Ile Val Pro Ala Asp Pro Thr Leu Trp Ser Thr Asp
        130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                    165                 170                 175

Lys Met Thr Lys Asp Asp Phe Gln Arg Leu Thr Pro Ser Tyr Asn Ala
                180                 185                 190

Asp Ile Leu Leu Ser His Leu His Tyr Leu Arg Glu Thr Pro Leu Pro
        195                 200                 205

His Leu Thr Ser Asp Asp Val Asp Lys Ala Leu Gln Asn Ser Pro Arg
210                 215                 220

Leu Met His Ala Arg Asn Thr Asp Leu Pro Tyr Glu Pro Pro Arg Arg
225                 230                 235                 240

Ser Ala Trp Thr Gly His Gly His Pro Thr Pro Gln Ser Lys Ala Ala
                    245                 250                 255

Gln Pro Ser Pro Ser Thr Val Pro Lys Thr Glu Asp Gln Arg Pro Gln
                260                 265                 270

Leu Asp Pro Tyr Gln Ile Leu Gly Pro Thr Ser Ser Arg Leu Ala Asn
        275                 280                 285

Pro Gly Ser Gly Gln Ile Gln Leu Trp Gln Phe Leu Leu Glu Leu Leu
        290                 295                 300

Ser Asp Ser Ser Asn Ser Ser Cys Ile Thr Trp Glu Gly Thr Asn Gly
305                 310                 315                 320

Glu Phe Lys Met Thr Asp Pro Asp Glu Val Ala Arg Arg Trp Gly Glu
                325                 330                 335

Arg Lys Ser Lys Pro Asn Met Asn Tyr Asp Lys Leu Ser Arg Ala Leu
                340                 345                 350

Arg Tyr Tyr Tyr Asp Lys Asn Ile Met Thr Lys Val His Gly Lys Arg
        355                 360                 365

Tyr Ala Tyr Lys Phe Asp Phe His Gly Ile Ala Gln Ala Leu Gln Pro
        370                 375                 380

His Pro Pro Glu Ser Ser Leu Tyr Lys Tyr Pro Ser Asp Leu Pro Tyr
385                 390                 395                 400

Met Gly Ser Tyr His Ala His Pro Gln Lys Met Asn Phe Val Ala Pro
                405                 410                 415

His Pro Pro Ala Leu Pro Val Thr Ser Ser Ser Phe Phe Ala Ala Pro
                420                 425                 430

Asn Pro Tyr Trp Asn Ser Pro Thr Gly Gly Ile Tyr Pro Asn Thr Arg
            435                 440                 445

Leu Pro Thr Ser His Met Pro Ser His Leu Gly Thr Tyr Tyr
    450                 455                 460
```